(12) United States Patent
Chen

(10) Patent No.: US 9,796,778 B1
(45) Date of Patent: Oct. 24, 2017

(54) ANTIBODIES AGAINST PATHOLOGICAL FORMS OF TDP-43 AND USES THEREOF

(71) Applicant: Academia Sinica, Taipei (TW)

(72) Inventor: Yun-Ru Chen, Taipei (TW)

(73) Assignee: Academia Sinica, Taipei (TW)

( * ) Notice: Subject to any disclaimer, the term of this patent is extended or adjusted under 35 U.S.C. 154(b) by 0 days.

(21) Appl. No.: 15/516,015

(22) PCT Filed: Sep. 15, 2015

(86) PCT No.: PCT/US2015/050114
§ 371 (c)(1),
(2) Date: Mar. 30, 2017

(87) PCT Pub. No.: WO2016/053610
PCT Pub. Date: Apr. 7, 2016

Related U.S. Application Data

(60) Provisional application No. 62/059,192, filed on Oct. 3, 2014.

(30) Foreign Application Priority Data

Mar. 9, 2015 (CN) ................................ 104107500

(51) Int. Cl.
*C07K 16/18* (2006.01)
*G01N 33/68* (2006.01)

(52) U.S. Cl.
CPC ......... *C07K 16/18* (2013.01); *G01N 33/6896* (2013.01); *C07K 2317/76* (2013.01); *G01N 2800/2821* (2013.01)

(58) Field of Classification Search
CPC ................ C07K 16/18; C07K 2317/76; G01N 33/6896; G01N 2800/2821
See application file for complete search history.

(56) References Cited

U.S. PATENT DOCUMENTS

2013/0219534 A1  8/2013  Wong et al.
2014/0255304 A1  9/2014  Roger et al.

FOREIGN PATENT DOCUMENTS

WO  WO 2009/007427 A2  1/2010
WO  WO 2010/003992 A1  1/2010

OTHER PUBLICATIONS

Chen 1995 "enhancement and destruction of antibody function by somatic mutation: unequal occurrence is controlled by v gene combinatorial associations" EMBO 14(12):2784-2794.*

* cited by examiner

*Primary Examiner* — Adam Weidner
(74) *Attorney, Agent, or Firm* — Muncy, Geissler, Olds & Lowe, P.C.

(57) ABSTRACT

Disclosed herein are novel pathological form of TDP-43, monoclonal antibodies against such pathological form of TDP-43, and uses thereof. The novel pathological form of TDP-43 is characterized in having a spherical particle size of about 2 to 400 nm in diameter.

11 Claims, 24 Drawing Sheets

V_H region

```
                                          CDR1
QVQLQQSGAE LAKPGASXKM SCXXXGYXFX XYWMHWXKQR
           CDR2
PGQGLEWIGY INPXTXXXEX NQXFKDXAXL TADXSSXTAY
                      CDR3
XQLXSLTSED SAVYXCXRGG KYXGGAMDY
```

V_L region

```
                                          CDR1
QIVLTXSPXX XSASPGEXVT XTCSAXSSVX YMHWXXQKPG
           CDR2
TSPKLWIXXT SNLASGVPAR FSGSGSGTSY SLTXSRMEAX
           CDR3
DAATYYCQQR SSYPLT
```

FIG 11

ANTIBODIES AGAINST PATHOLOGICAL FORMS OF TDP-43 AND USES THEREOF

BACKGROUND OF THE INVENTION

1. Field of the Invention

The present disclosure relates to novel pathological form of transactivation responsive (TAR)-DNA-binding protein 43 kDa (TDP-43), antibodies against such pathological form of TDP-43, and uses thereof.

2. Description of Related Art

Neurodegenerative diseases have become an important health issue in the modern society. According to the report of WHO, more than 75% of elder population in the world will suffer some kinds of neurodegenerative disease in the year of 2025. Frontotemporal lobar degeneration (FTLD) is the second most common form of dementia in the USA in the people age less than 65, and transactivation responsive (TAR)-DNA-binding protein of 43 kDa (TDP-43) was identified to be the major disease protein in the majority of sporadic and familial FTLD cases, as well as amyotrophic lateral sclerosis (ALS). In addition, TDP-43 was present in up to 57% of patients in Alzheimer's disease. Currently, there is no cure or treatment for these diseases, and significant efforts have been made to identify molecules that may modulate the formation of pathological forms of TDP-43.

In view of the foregoing, there exist in the related art, a need for identifying molecules that may modulate the pathological forms of TDP-43, such molecules will be potential drug candidates for the manufacture of a medicament for the prophylaxis or treatment of neurodegenerative diseases resulted from the formation of pathological forms of TDP-43.

SUMMARY

This invention is based on the finding that transactivation responsive (TAR)-DNA-binding protein 43 kDa (TDP-43) oligomer are capable of cross-seeding Alzheimer's amyloid-β (Aβ) to form amyloid oligomers, and are neurotoxic in vitro and in vivo. Accordingly, a molecule capable of binding (e.g., an antibody) such TDP-43 oligomer may suppresses the TDP-43 proteinopathy and thus are useful for the manufacture of a medicament (i.e., a vaccine and passive immunization) suitable for diagnosing, preventing or treating a neurodegenerative disease resulted from deposit of pathological form of TDP-43.

Accordingly, the present disclosure aims to provide an antibody or a fragment thereof that specifically binds to TDP-43 oligomer. The antibody comprises a heavy chain variable region comprising amino acid sequences of SEQ ID NO: 1, SEQ ID NO: 2 and SEQ ID NO: 3; and a light chain variable region comprising amino acid sequences of SEQ ID NO: 5, SEQ ID NO: 6 and SEQ ID NO: 7.

The TDP-43 is characterized with a particle size of about 2 to 400 nm in diameter. Preferably, TDP-43 oligomer has a spherical particle size of about 40 to 60 nm in diameter.

According to some preferred embodiments, the heavy chain variable region of the present antibody has the amino acid sequence of SEQ ID NO: 4, and the light chain variable region of the present antibody has the amino acid sequence of SEQ ID NO: 8.

In one example, the present antibody is produced by the hybridoma cell line deposited in the Bioresource and Collection Center (BCRC) of the Food Industry Development and Research Institute (FIDRI) in Taiwan (HsinChu, Taiwan, R.O.C.) as accession number of BCRC960494.

In another example, the present antibody is produced by the hybridoma cell line deposited with the BCRC as accession number of BCRC960495.

In still another example, the present antibody is produced by the hybridoma cell line deposited with the BCRC as accession number of BCRC960496.

In a further example, the present antibody is produced by the hybridoma cell line deposited with the BCRC as accession number of BCRC960497.

In still a further example, the present antibody is produced by the hybridoma cell line deposited with the BCRC as accession number of BCRC960498.

It is therefore the second aspect of this disclosure to provide a use of the antibody as described above for manufacturing a medicament or a pharmaceutical composition for the prophylaxis or treatment of a TDP-43 oligomer associated disease. The medicament or the pharmaceutical composition comprises an effective amount of the antibody described above; and a therapeutically acceptable excipient.

According to preferred embodiments of the present disclosure, the present antibody comprises a heavy chain variable region comprising amino acid sequences of SEQ ID NO: 1, SEQ ID NO: 2 and SEQ ID NO: 3; and a light chain variable region comprising amino acid sequences of SEQ ID NO: 5, SEQ ID NO: 6 and SEQ ID NO: 7. In one specific example, the heavy chain variable region has the amino acid sequence of SEQ ID NO: 4, and the light chain variable region has the amino acid sequence of SEQ ID NO: 8.

According to other preferred embodiments, the antibody may be produced by any of the hybridoma cell lines deposited with the BCRC as accession number of BCRC960494, BCRC960495, BCRC960496, BCRC960497, or BCRC960498.

The antibody of this invention is present at a level of about 0.1° A to 99% by weight, based on the total weight of the pharmaceutical composition. In some embodiments, the antibody of this invention is present at a level of at least 1% by weight, based on the total weight of the pharmaceutical composition. In certain embodiments, the antibody of this invention is present at a level of at least 5% by weight, based on the total weight of the pharmaceutical composition. In still other embodiments, the antibody of this invention is present at a level of at least 10% by weight, based on the total weight of the pharmaceutical composition. In still yet other embodiments, the antibody of this invention is present at a level of at least 25% by weight, based on the total weight of the pharmaceutical composition.

The TDP-43 oligomer associated disease treatable by the medicament or the pharmaceutical composition of the present disclosure may be any of, Alzheimer's disease, argyrophilic grain disease, amyotrophic lateral sclerosis (ALS), ALS-parkinsonism dementia complex of Guam, vascular dementia, frontotemporal dementia, semantic dementia, dementia with Lewy bodies, Huntington's disease, Spinocerebellar ataxia, inclusion body myopathy, inclusion body myositis, hippocampal sclerosis, or Parkinson's disease.

It is therefore a third aspect of the present disclosure to provide a method for the prophylaxis or treatment of a TDP-43 oligomer associated disease in a subject. The method includes the step of, administering to the subject a therapeutically effective amount of the antibody of this invention, so as to inhibit or suppress the TDP-43 proteinopathies.

According to some preferred embodiments, the present antibody comprises a heavy chain variable region comprising amino acid sequences of SEQ ID NO: 1, SEQ ID NO: 2 and SEQ ID NO: 3; and a light chain variable region comprising amino acid sequences of SEQ ID NO: 5, SEQ ID NO: 6 and SEQ ID NO: 7. In one specific example, the heavy chain variable region has the amino acid sequence of SEQ ID NO: 4, and the light chain variable region has the amino acid sequence of SEQ ID NO: 8.

According to other preferred embodiments, the antibody may be produced by the hybridoma cell line deposited with the BCRC as accession number of BCRC960494, BCRC960495, BCRC960496, BCRC960497, or BCRC960498.

The TDP-43 oligomer associated disease that may be treated by the method of the present disclosure is Alzheimer's disease (AD), argyrophilic grain disease, amyotrophic lateral sclerosis (ALS), ALS-parkinsonism dementia complex of Guam, vascular dementia, frontotemporal dementia, semantic dementia, dementia with Lewy bodies, Huntington's disease, Spinocerebellar ataxia, inclusion body myopathy, inclusion body myositis, hippocampal sclerosis, or Parkinson's disease (PD).

It is the fourth aspect of the present disclosure to provide a method for the diagnosis of a TDP-43 oligomer associated disease in a subject. The method includes steps of, obtaining a biological sample from the subject; determining the amount of the TDP-43 oligomer in the biological sample by contacting the biological sample with an effective amount of the antibody of this invention; and comparing the detected amount of the TDP-43 oligomer in the biological sample with that of a control sample obtained from a healthy subject; wherein a significantly higher or lower amount of the detected TDP-43 oligomer in the biological sample than that of the control sample indicates that the subject suffers from the neurodegenerative disease.

According to preferred embodiments of the present disclosure, the biological sample is brain biopsy sample, a cerebrospinal fluid sample, a whole blood sample, a serum sample, a plasma sample, a urine sample, or a mucus sample.

According to some preferred embodiments, the present antibody comprises a heavy chain variable region comprising amino acid sequences of SEQ ID NO: 1, SEQ ID NO: 2 and SEQ ID NO: 3; and a light chain variable region comprising amino acid sequences of SEQ ID NO: 5, SEQ ID NO: 6 and SEQ ID NO: 7. In one specific example, the heavy chain variable region has the amino acid sequence of SEQ ID NO: 4, and the light chain variable region has the amino acid sequence of SEQ ID NO: 8.

According to other preferred embodiments, the antibody may be produced by any of the hybridoma cell lines deposited with the BCRC as accession number of BCRC960494, BCRC960495, BCRC960496, BCRC960497, or BCRC960498.

It is therefore the fifth aspect of the present disclosure to provide a kit for the detection of a pathological form of TDP-43 in a biological sample. The detecting result may be used as a reference for determining whether a subject of the biological sample suffers from a TDP-43 oligomer associated disease. The kit includes, at least, a container, and reagents for detecting TDP-43 oligomer in the biological sample, wherein the reagents comprise the anti-TDP-43 oligomer antibody of this invention and a legend associated with the container and indicating how to use the anti-TDP-43 oligomer antibody of this invention for detecting the pathological form of TDP-43 (i.e., TDP-43 oligomer as described herein) in the biological sample. The legend may be in a form of pamphlet, tape, CD, VCD or DVD. The kit may further include a negative control that indicates either absence of TDP-43 oligomer or the normal level of the TDP-43 oligomer in a healthy subject.

The details of one or more embodiments of the invention are set forth in the accompanying description below. Other features and advantages of the invention will be apparent from the detail descriptions, and from claims.

BRIEF DESCRIPTION OF THE DRAWINGS

The present description will be better understood from the following detailed description read in light of the accompanying drawings, where:

FIG. 1A: Analytical size-exclusion chromatography (SEC) of full-length TDP-43 purified from *E. coli* monitored by absorption at 280 nm (solid line) or human HEK293 cells quantified by slot blotting intensity (dashed line). The retention times of the molecular weight standards are indicated. FIG. 1B: Dot blotting of TDP-43 using anti-amyloid oligomer antibody, A11. Freshly purified TDP-43 before (pre-load TDP-43) and after SEC (the void volume, TDP-43 oligomers) and the buffers were immunostained with A11. FIG. 1C: Freshly purified TDP-43 was dotted in buffer or buffers containing 9 M urea, 7.2 M GdnHCl, or 2% SDS with or without heating at 90° C. for 1 h. Three replicates were generated and probed separately by A11 antibody, anti-N-terminal TDP-43 antibody (residues 1-260), and anti-C-terminal TDP-43 antibody (residues 250-414). FIG. 1D: TEM image of TDP-43 oligomers (scale bar, 500 nm) and zoomed-in images of a single oligomer are shown in the upper left (scale bar, 50 nm). FIG. 1E: AFM image of TDP-43 oligomers (scale bar, 500 nm) and zoomed-in images of a single oligomer are shown in the upper left (scale bar, 50 nm). FIGS. 1F and 1G: DLS analysis of the oligomer fraction of TDP-43 from SEC. Particle diameters are plotted against scattered light intensity and particle number.

FIG. 2A: Far-UV CD spectra of full-length TDP-43 (solid line) and short-form TDP-43 (dashed line). The spectra from 250 to 190 nm are shown. FIG. 2B: Bis-ANS fluorescence spectra of full-length TDP-43 (solid line) and short-form TDP-43 (dashed line). The buffer signal is shown (dotted line). FIG. 2C: ThT binding of TDP-43 in comparison to Aβ fibrils. The ThT fluorescence emission spectra of full-length TDP-43 (■, solid line), short-form TDP-43 (●, dashed line), and Aβ fibrils (▲, dotted line). Only Aβ fibrils showed ThT binding signal. FIG. 2D: TAR DNA binding of TDP-43 monitored by fluorescence titration. Full-length (squares) and short-form (circles) of TDP-43 were titrated with single strand TAR DNA-A (solid symbols) and -B sites (empty symbols). The emission maxima of TDP-43 or TDP-43s at 350 nm were monitored while exciting at 280 nm. The data shown were normalized to the starting point and the lines shown are fit lines.

FIG. 3A: ThT assay of Aβ fibrillization without and with TDP-43 in concentrations ranging from 0.4 to 4%. Percentages of TDP-43 seeded in molar ratio are indicated. FIG. 3B: Photo-induced cross-linking (PICUP) assay of Aβ without and with TDP-43 at time 0. The percentages of TDP-43 seeded in molar ratio are indicated. FIG. 3C: TEM images of end-point products of Aβ without and with 4% TDP-43 (scale bar, 100 nm).

FIG. 4C: Cytotoxicity of TDP-43 to primary neuronal cultures using MTT assay. Cell viability in MTT assays is normalized against the buffer control (n=3, mean±standard deviation). The statistics was analyzed by one way-ANOVA with Tukey post-test for FIG. 4A and FIG. 4C and two tailed, unpaired Student's t-test for FIG. 4B ($*p<0.05$, $p<0.01$, $*p<0.001$). FIG. 4D: The immunocytochemistry of primary neurons treated with control or TDP-43, 0.44 µM. The samples were subjected to MAP-2 immunostaining, GFAP immunostaining, and DAPI staining. FIG. 4E: Intrahippocampal TDP-43 injection showed neuronal loss in the CA regions of mouse hippocampus. Hippocampal injections (n=3 each group) of the buffer control and TDP-43 were performed. Immunohistochemistry of the hippocampal regions with neuronal specific marker NeuN and nuclear specific dye DAPI are shown. The lesions are indicated by arrows (scale bar, 50 µm).

FIG. 5A: Freshly purified TDP-43 in native buffer or buffers containing 9 M urea, 7.2 M GdnHCl, or 2% SDS with or without heating at 90° C. for 1 h was subjected to dot blotting probed by the newly generated polyclonal antibody, TDP-O, using TDP-43 oligomers as immunogen. The immunoreactivity of TDP-43 conformation by TDP-O was similar to that by A11 as shown in FIG. 1C. FIG. 5B: Aβ oligomers were subjected to dot blotting probed by A11 and TDP-O antibodies. A11, but not TDP-O, was able to recognize Aβ oligomers. FIG. 5C: TDP-43 with (solid line) and without (dotted line) 3 fold concentration were subjected to SEC. The elution volumes of TDP-43 oligomer (★), TDP-43 monomer (☆), and the molecular weight standards are indicated. FIG. 5D: The 1 ml SEC fractions were collected and subjected to dot blotting by TDP-O (upper blot) and $N_{1-260}$ antibodies (lower blot). FIG. 5E: The purified TDP-43 oligomers and monomers from SEC were characterized by ELISA. The TDP-43 samples were coated dose-dependently onto the ELISA plates. The TDP-43 oligomers were probed by TDP-O (■) and $N_{1-260}$ (□) antibodies and TDP-43 monomers were probed by TDP-O (●) and $N_{1-260}$ (○) antibodies. TDP-O antibody possesses significant higher specificity against TDP-43 oligomers.

FIG. 6A: Immunofluorescent staining of human TDP-43 and TDP-43 oligomers in the brain slices of wild type and 6- and 12-month-old TDP-43 $Tg^{+/+}$ transgenic mice. Cells with anti-TDP oligomer staining, TDP-43 staining, and DAPI staining are shown (scale bar, 100 µm). Blocked area was presented at higher magnification in the last column (scale bar, 25 µm). FIG. 6B: Quantified results showed that the ratio of cells with deposition of TDP-O and TDP-43 in cytosol were age dependent. (n=3 per group, random 5 views were calculated for each mouse, data represent as mean±S.E.M. The statistics was analyzed by one way-ANOVA with Turkey post-test ($*p<0.05$, $p<0.01$, $*p<0.001$).

FIG. 8A: TDP-43 oligomers in FTLD-TDP (scale bar, 100 nm). FIG. 8B: zoom-in images of TDP-43 oligomers (scale bar, 50 nm).

FIG. 10A: TDP-43 oligomers and monomers were separated and collected by Superdex 200 10/300 GL column. FIG. 10B: Conditional medium of TDP-O-3, -5, -8, -9, and -10 hybridoma cell lines were used to detect the TDP-43 oligomers and monomers by ELISA assay.

FIG. 11 depicts the consensus amino acid sequences of heavy chain variable region ($V_H$) and light chain variable region ($V_L$) of the 5 isolated TDP-O monoclonal antibodies. X represents any amino acid residues, and CDR is the abbreviation of the complementarity determining region. Seq ID NOs: 4 and 8.

DESCRIPTION

Figure 1A:
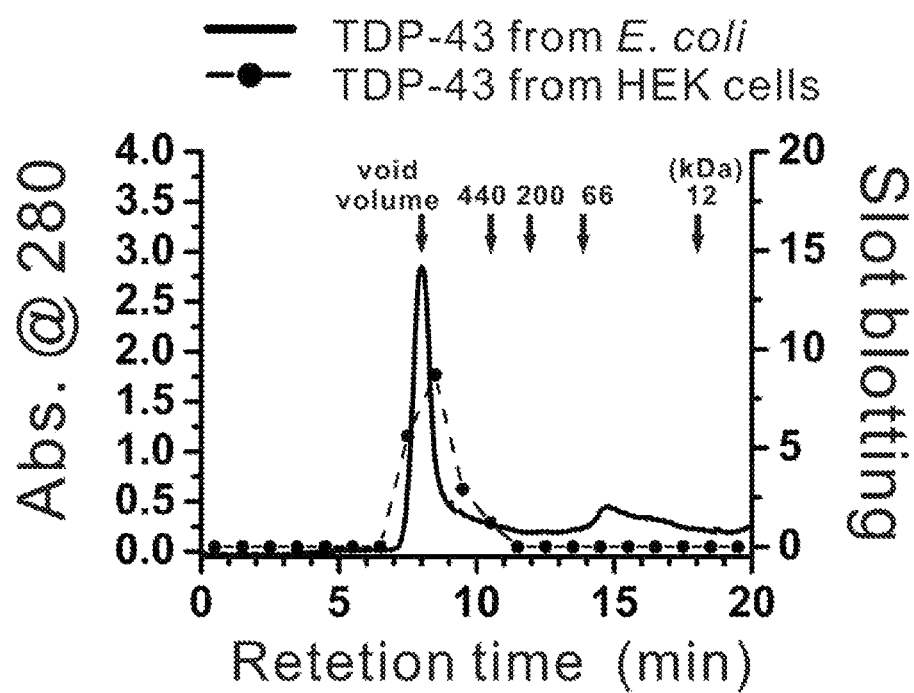
FIGS. 1A-1G depict that full-length TDP-43 forms amyloid-like oligomers.

The detailed description provided below in connection with the appended drawings is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples.

I. Definition

The term "TDP-43 proteinopathy" as used herein refers to diseases particularly linked to transactivation responsive (TAR)-DNA-binding protein of 43 kDa (TDP-43). TDP-43 is a disease protein known to link with frontotemporal lobar degeneration with ubiquitin-positive inclusion (FTLD-U), and amyotrophic lateral sclerosis (ALS). TDP-43 proteinopathy thus includes, but is not limited to, Alzheimer's disease (AD), argyrophilic grain disease, amyotrophic lateral sclerosis (ALS), ALS-parkinsonism dementia complex of Guam, vascular dementia, frontotemporal dementia, semantic dementia, dementia with Lewy bodies, Huntington's disease, Spinocerebellar ataxia, inclusion body myopathy, inclusion body myositis, hippocampal sclerosis, or Parkinson's disease (PD).

The term "an effective amount" as used herein refers to an amount effective, at dosages, and for periods of time necessary, to achieve the desired therapeutically result with respect to the treatment of a TDP-43 oligomer associated disease.

The phrase "pharmaceutically acceptable" refers to molecular entities and compositions that are "generally regarded as safe", e.g., that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans.

The term "administered", "administering" or "administration" are used interchangeably herein to refer means either directly administering a bi-specific antibody or a composition of the present disclosure.

The term "subject" or "patient" refers to an animal including the human species that is treatable with the compositions and/or methods of the present disclosure. The term "subject" or "patient" intended to refer to both the male and female gender unless one gender is specifically indicated. Accordingly, the term "subject" or "patient" comprises any mammal which may benefit from treatment of cancer. Examples of a "subject" or "patient" include, but are not limited to, a human, rat, mouse, guinea pig, monkey, pig, goat, cow, horse, dog, cat, bird and fowl. In an exemplary embodiment, the patient is a human.

The term "treat" or "treatment" as used herein are intended to mean obtaining a desired pharmacological and/ or physiologic effect, e.g., detecting the presence of pathologic form of TDP-43, preventing or rescuing organ atrophy, or inhibiting development of dementia or muscular weakness and stiffness. The effect may be prophylactic in terms of completely or partially preventing a disease or symptom thereof and/or therapeutic in terms of a partial or complete cure for a disease and/or adverse effect attributable to the disease. "Treatment" as used herein includes preventative (e.g., prophylactic), curative or palliative treatment of a disease in a mammal, particularly human; and includes: (1) preventative (e.g., prophylactic), curative or palliative treatment of a disease or condition (e.g., a cancer or heart failure) from occurring in an individual who may be pre-disposed to the disease but has not yet been diagnosed as having it; (2) inhibiting a disease (e.g., by arresting its development); or (3) relieving a disease (e.g., reducing symptoms associated with the disease).

The term "antibody" or "antibodies" is used in the broadest sense and specifically covers monoclonal antibodies, polyclonal antibodies, multispecific antibodies (e.g., bi-specific antibodies), and antibody fragments so long as they exhibit the desired biological activity, that is, to specifically bind to an antigen when it preferentially recognizes its target antigen in a complex mixture of proteins and/or other molecules. According to one embodiment of the present application, the antibody of this invention is a polyclonal antibody that specifically recognizes TDP-43 oligomer.

The term "monoclonal antibody" as used herein refers to an antibody obtained from a population of substantially homogeneous antibodies, and is not to be constructed as requiring production of the antibody by any particular method. In contrast to polyclonal antibodies which typically include different antibodies directed to different epitopes, each monoclonal antibody is directed against a single determinant (i.e., epitope) on the antigen. The monoclonal antibodies of the present disclosure may be made by hybridoma method or by recombinant DNA methods. The monoclonal antibodies herein specifically include "chimeric" or "recombinant" antibodies, in which a portion of the heavy and/or light chain is identical with or homologous to corresponding sequences in antibodies derived from a particular species or belonging to a antibody class or subclass, while the remainder of the chain identical with or homologous to corresponding sequences in antibodies derived from another species or belonging to another antibody class or subclass, as well as fragments of such antibodies, as long as they exhibit the desired biological activity.

"Humanized" forms of non-human (e.g., murine) antibodies are chimeric antibodies which contain minimal sequence derived from non-human immunoglobulin. Humanized antibodies are human immunoglobulins in which hypervariable region residues are replaced by hypervarible region residues from a non-human species such as mouse, rat, rabbit, or non-human primate having the desired specificity or affinity. In some instances, Fv framework region (FR) residues of the human immunoglobulin are replaced by corresponding non-human residues. In general, the humanized antibody will comprise substantially all of at least one, and typically two, variable domains, in which all or substantially all of the FR regions are those of a human immunoglobulin sequence. The humanized antibody may optionally comprise at least a portion of an immunoglobulin constant region (Fc), typically that of a human immunoglobulin.

The singular forms "a", "and", and "the" are used herein to include plural referents unless the context clearly dictates otherwise.

II. Description of the Invention

Transactivation responsive (TAR)-DNA-binding protein of 43 kDa (TDP-43) has been identified as the disease protein in ubiquitinated misfolded aggregates of all subtypes of sporadic frontotemporal lobar degeneration with ubiquitin-positive inclusion (FTLD-U), as well as amyotrophic lateral sclerosis (ALS). In the present study, inventors unexpectedly discovered that full length TDP-43 forms structurally stable spherical oligomers that cross-seed Alzheimer's amyloid-β (Aβ) to form amyloid oligomers, thus if an agent (e.g., an antibody) could bind such TDP-43 oligomer, such agent may suppress or inhibit TDP-43 proteinopathy and/or TDP-43 effect to a subsequent event such as, but not limited to, Aβ oligomerization, and accordingly is useful for the manufacture of a medicament (e.g., a vaccine or passive immunization) suitable for preventing or treating a neurodegenerative disease resulted from the deposit and/or aggregation of pathological form of TDP-43.

Accordingly, it is the first aspect of the present disclosure to provide an antibody, particularly, an antibody that recognizes the TDP-43 oligomer identified in the examples of the present invention, thereby inhibits the aggregation of a protein, particularly, TDP-43, which aggregation is associated with a disease. In general, the protein aggregation process proceeds in a self-propagating manner, once initiated, an aggregation cascade ensues that involves induced conformation change and/or polymerization of further protein molecules, leading to the formation of toxic product that is resistant to proteolysis. The thus formed protein aggregation is thought to be the proximal cause of neurodegeneration diseases, such as Alzheimer's disease (AD), argyrophilic grain disease, amyotrophic lateral sclerosis (ALS), ALS-parkinsonism dementia complex of Guam, vascular dementia, frontotemporal dementia, semantic dementia, dementia with Lewy bodies, Huntington's disease, Spinocerebellar ataxia, inclusion body myopathy, inclusion body myositis, hippocampal sclerosis, or Parkinson's disease (PD).

According to preferred embodiment of the present disclosure, the TDP-43 oligomer is characterized in having a particle size of about 2 to 400 nm in diameter. Preferably, the TDP-43 oligomer has a particle size of about 20 to 400 nm in diameter, such as 20 to 30 nm, 30 to 40 nm, 40 to 50 nm, 50 to 60 nm, 60 to 70 nm, 70 to 80 nm, 80 to 90 nm, 90 to 100 nm, 100 to 120 nm, 120 to 140 nm, 140 to 160 nm, 160 to 180 nm, 180 to 200 nm, 200 to 220 nm, 220 to 240 nm, 240 to 260 nm, 260 to 280 nm, 280 to 300 nm, 300 to 320 nm, 320 to 340 nm, 340 to 360 nm, 360 to 380 nm, and 380 to 400 nm in diameter. More preferably, the TDP-43 oligomer has a spherical particle size of about 40 to 60 nm in diameter.

The antibodies of the present invention specifically bind the TDP-43 oligomer described above, its epitopes, as well as various conformations and epitopes thereof. In preferred embodiments, antibodies disclosed herein preferentially bind pathologic TDP-43, specifically, full-length TDP-43 oligomer characterized in having a spherical particle size of about 2 to 400 nm in diameter.

To produce the desired monoclonal antibodies, animals such as mice, rats or rabbits are first immunized with TDP-43 oligomer at a suitable dose. Generally, adjuvant and the TDP-43 oligomer solution are mixed together when immunizing the animals with TDP-43 oligomer. Examples of adjuvants useful for this invention include Freund's complete adjuvant (FCA), Freund's incomplete adjuvant (FIA), and aluminum hydroxide adjuvant. Immunization is generally carried out mainly by intravenous, subcutaneous, intraperitoneal or intramuscular injection of the antigen. The immunization interval is not particularly limited. Immunization may be carried out at intervals of several days to several weeks, preferably 2 to 3 weeks, for 1 to 10 times, preferably 2 to 5 times. Once antibody titers reaches 2 or more in the absorbance level as the result of immunization, the animals are left for about 1 month. Then, re-immunization is carried out for at least once. Several days, preferably 3 to 5 days, after the final immunization, splenic cells and regional lymph nodes are removed. Blood samples are taken regularly after immunization and subject to centrifugation to separate sera. The resultant sera are then subject to measurement of antibody titers by any suitable method, which includes, and is not limited to, enzyme linked immunosorbent assay (ELISA), enzyme immunoassay (EIA), or radio immunoassay (RIA). In one preferred example, antibody titers are measured by ELISA. Then, final immunization is given to those animals showing high antibody titers to TDP-43 oligomer.

Antibody-producing cells are prepared from splenic cells and regional lymph nodes or the like of the immunized animals. In the preparation of antibody-producing cells, it is preferably to remove tissue debris and erythrocytes as much as possible. Commercial erythrocyte remover may be used to this purpose. Alternatively, a buffer ammonium chloride and Tris may be prepared and used. The thus prepared antibody-producing cells are immediately fused with immortal cells such as myeloma cells to produce hybridoma cells, which semi-eternally continue to proliferate while producing antibodies. Commonly available cell strain derived from an animal such as mouse may be used. A preferable cell strain to be used in this invention should be those that fuse efficiently, support stable high level production of antibody and are sensitive to HAT selection medium, which contains hypoxanthine, thymidine and aminopterin, and should survive there only when fused with antibody-producing cells. Examples of myeloma cells include, but are not limited to, mouse myeloma cell line (such as myeloma FO cells) and human myeloma cell line (such as Karpas 707H).

Cell fusion is usually carried out by mixing splenic cells or lymph node cells with a commercial available myeloma cells in the presence of a cell-fusion promoter, such as PEG having an average molecular weight from about 200 to 20,000 daltons or the like. Alternatively, cell fusion may be carried out in a commercial cell fusion device utilizing electric stimulation such as electro-fusion. After the fusion, the resultant cells are then diluted and cultured in HAT medium.

Hybridomas of interest are then selected from the fused cells. The fused cells surviving cultured in HAT medium would form colonies. The supernatant of each culture well is then collected and examine for the presence or absence of antibody titers to TDP-43 oligomer. As a method of confirmation, ELISA, EIA or RIA may be used, in which TDP-43 oligomer or TDP-43 monomer is coated onto the plates and used as a screening criteria. Once antibody-positive wells are identified, cells are then cultured in a HT medium, which does not contain aminopterin. After culturing for a while, antibody titers in the culture supernatant are confirmed again. Cells that are finally selected are then subject to cloning to obtain single cells. Clones that exhibit high specificity to TDP-43 oligomer are selected, and are proliferated to some extent to establish hybridomas.

According to preferred embodiments of the present disclosure, 5 hybridomas, TDP-O-3, TDP-O-5, TDP-O-8, TDP-O-9 and TDP-O-10, were selected, and monoclonal antibodies may be isolated or prepared by any known method. For example, antibodies may be prepared from cultured supernatant obtained by culturing hybridomas in a medium with low serum concentration. Alternatively, hybridomas may be injected into abdominal cavities of animals and the resultant abdominal dropsies are collected to prepare antibodies. Antibodies may be purified or isolated by methods that employ affinity column, gel filtration chromatography, ion exchange chromatography or the like. Any of these known methods may be appropriately selected or used in combination.

According to specific embodiments, the monoclonal antibodies of the present disclosure are respectively produced by the hybridoma cell line TDP-O-3, TDP-O-5, TDP-O-8, TDP-O-9 and TDP-O-10, which are deposited in the Bioresource Collection and Research Center (BCRC) of the Food Industry Development and Research Institute (FIDRI) (HsinChu, Taiwan, R.O.C.) as accession number of BCRC960494, BCRC960495, BCRC960496, BCRC960497, or BCRC960498.

According to preferred embodiments, the monoclonal antibodies disclosed herein comprise consensus sequences respectively located at the heavy and light chain variable regions. Accordingly, the monoclonal antibodies described herein respectively comprise a heavy chain variable region comprising amino acid sequences of SEQ ID NO: 1, SEQ ID NO: 2 and SEQ ID NO: 3; and a light chain variable region comprising amino acid sequences of SEQ ID NO: 5, SEQ ID NO: 6 and SEQ ID NO: 7. Preferably, the humanized monoclonal antibody comprises a heavy chain variable region of SEQ ID NO: 4, and a light chain variable region of SEQ ID NO: 8. Among the amino acid sequences described in the present disclosure, particularly SEQ ID NOs: 1 to 6, and 8, Xaa represents any L- or D-form amino acid residues known in the art. In one example, Xaa is an acidic amino acid residue (e.g., aspartate or glutamate). In another example, Xaa is a basic amino acid residue (e.g., lysine, arginine, or histidine). In a further example, Xaa is a nonpolar amino acid residue (e.g., alanine, valine, leucine, isoleucine, proline, phenylalanine, methionine, or tryptophan). In still another example, Xaa is an uncharged polar amino acid residue (e.g., glycine, asparagine, glutamine, cysteine, serine, threonine, or tyrosine).

Alternatively, anti-TDP-43 oligomer monoclonal antibodies may be produced by DNA cloning or DNA synthesis. DNA encoding anti-TDP-43 oligomer mAbs may be easily isolated and sequenced by use of conventional procedures, such as using oligonucleotide probes that are capable of binding specifically to genes encoding the heavy and light chains of the monoclonal antibodies. The hybridoma cells (e.g., TDP-O-3, TDP-O-5, TDP-O-8, TDP-O-9 or TDP-O-10 hybridoma) serve as a preferred source of such DNA. Once isolated, the DNA may be placed into expression vectors, which are then transfected into host cells such as *E. Coli* cells, simian COS cells or Chinese hamster ovary (CHO) cells or myeloma cells that do not produce immunoglobulin proteins, to synthesize the desired monoclonal antibodies in the recombinant host cells.

The monoclonal antibodies thus produced and the DNA encoding such antibodies can then be used to produce chimeric antibodies (e.g., bi-specific antibodies), humanized antibodies and/or antibody fragments derived thereof.

The major concern of a non-human origin monoclonal antibody is its immunogenicity to the recipient, in some cases, caused dangerous allergic reactions. Most monoclonal antibodies are of murine origin, and have been found to be immunogenic when injected to human. To reduce the immunogenicity of anti-TDP-43 oligomer mAbs of this invention, humanized antibodies are produced by attaching variable domains in the heavy and light chains of murine anti-TDP-43 oligomer Abs onto the constant regions of human antibodies.

To create humanized anti-TDP-43 oligomer antibodies, the DNA encoding such antibodies was isolated and sequenced, and then used to create humanized constructs.

According to preferred embodiments of the present disclosure, CDR (complementary determining region) grafting is employed, in which the CDR regions in the VH and VL genes of a human antibody are replaced with the appropriate CDR coding segments (such as those DNA segments in anti-TDP-43 oligomer Abs that code amino acid segments responsible for binding TDP-43 oligomer). The resulting antibodies therefore have variable regions in which only the CDRs are from the original mouse antibodies, while the framework regions in the VH and VL genes as well as the constant region genes (i.e., CK or CH1-H-CH2-CH3) are those of human IgG.

In preferred embodiments, the humanized anti-TDP-43 oligomer mAb comprises a heavy chain variable domain and a light chain variable domain. Once produced, the humanized anti-TDP-43 oligomer mAbs may be purified according to standard procedures in the art, including cross-flow filtration, affinity column chromatography, gel filtration and the like. It should be understood that the humanized antibodies shall perform in a manner identical or substantially similar to that of murine anti-TDP-43 oligomer Abs. Preferably, the humanized anti-TDP-43 oligomer Abs (either in the form of Fab or full length IgG) shall be more advantages to use in a human subject, as compared to the murine version. In some embodiments, the humanized anti-TDP-43 oligomer Abs are used in the production of bi-specific antibodies of the present disclosure.

Anti-TDP-43 oligomer antibodies of the present invention can be characterized by use of any in vivo or in vitro models of TDP-43 proteinopathies. A skilled artisan readily understands that an anti-TDP-43 oligomer antibody of the present invention can be characterized in a mouse model, such as the animal model described in Example 7. Alternatively, the anti-TDP-43 oligomer antibody of the present invention can be characterized by human AD samples as described in Example 8.

According to the in vitro data described in one example, the anti-TDP-43 oligomer antibody of the present invention possesses an inhibitory effect on the cell cytotoxicity induced by TDP-43 oligomers. According to the example, the concentration of the present anti-TDP-43 oligomer antibody sufficient to inhibit the TDP-43 oligomer-induced cytotoxicity is about 0.001-5.0 mg/m I; for example, 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.5, 2.0, 2.5, 3.0, 3.5, 4.0, 4.5, or 5.0 mg/ml. Preferably, the concentration is about 0.01-1.0 mg/ml. More preferably, the concentration is about 0.02-0.08 mg/ml.

A skilled artisan understands that an experimental model of TDP-43 proteinopathy can be used in a preventive setting or in a therapeutic setting. In a preventive setting, the dose of animals starts prior to the onset of the TDP-43 proteinopathy or symptoms thereof, and the Anti-TDP-43 oligomer antibody of the present invention is evaluated for its ability to prevent, reduce or delay the onset of TDP-43 proteinopathy or symptoms thereof. In a therapeutic setting, the dose of animals starts after the onset of the TDP-43 proteinopathy or symptoms thereof, and the Anti-TDP-43 oligomer antibody of the present invention is evaluated for its ability to treat, reduce or alleviate the onset of TDP-43 proteinopathy or symptoms thereof. Symptoms of TDP-43 proteinopathy include, but are not limited to, accumulation of pathological TDP-43 deposits in the brain, spinal cord, cerebrospinal fluid or serum of a test subject.

Accordingly, the disclosure provides a pharmaceutical composition or a medicament for treating a neurodegenerative disease associated with the aggregation of Aβ. The composition comprises an effective amount of the anti-TDP-43 oligomer antibody of the present invention as described herein; and a pharmaceutically acceptable excipient. The TDP-43 oligomer associated disease treatable by the pharmaceutical composition or the medicament of the present disclosure includes, but is not limited to, Alzheimer's disease, argyrophilic grain disease, amyotrophic lateral sclerosis (ALS), ALS-parkinsonism dementia complex of Guam, vascular dementia, frontotemporal dementia, semantic dementia, dementia with Lewy bodies, Huntington's disease, Spinocerebellar ataxia, inclusion body myositis, inclusion body myositis, hippocampal sclerosis, or Parkinson's disease.

Generally, the anti-TDP-43 oligomer antibody of this invention is present at a level of about 0.1% to 99% by weight, based on the total weight of the pharmaceutical composition. In some embodiments, the anti-TDP-43 oligomer antibody of this invention is present at a level of at least 1% by weight, based on the total weight of the pharmaceutical composition. In certain embodiments, the anti-TDP-43 oligomer antibody is present at a level of at least 5% by weight, based on the total weight of the pharmaceutical composition. In still other embodiments, the anti-TDP-43 oligomer antibody is present at a level of at least 10% by weight, based on the total weight of the pharmaceutical composition. In still yet other embodiments, the anti-TDP-43 oligomer antibody) is present at a level of at least 25% by weight, based on the total weight of the pharmaceutical composition.

In some embodiments, the medicament of said pharmaceutical composition of this invention further includes an agent that is known to improve the symptoms of a neurodegenerative disease. Examples of such agent include, and are not limited to, AChEI, an Aβ inhibitor, or a muscarinic receptor agonist, and the like.

The medicament or said pharmaceutical composition is prepared in accordance with acceptable pharmaceutical procedures, such as described in Remington's Pharmaceutical Sciences, 17$^{th}$ edition, ed. Alfonoso R. Gennaro, Mack Publishing Company, Easton, Pa. (1985). Pharmaceutically acceptable excipients are those that are compatible with other ingredients in the formulation and biologically acceptable.

The anti-TDP-43 oligomer antibody of this invention may be administered by any means known in the art, such as orally, intraperitoneally, intracranially, intrathecally, intramuscularly, intraveneously, transdermally, rectally or by inhalation, alone or in combination with conventional pharmaceutically acceptable excipients. In one preferred embodiment, the anti-TDP-43 oligomer antibody of this invention is administered intraveneously to the subject. In another preferred embodiment, the anti-TDP-43 oligomer antibody of this invention is administered intrathecally to the subject.

Applicable solid excipients may include one or more substances that may also act as flavoring agents, lubricants, solubilizers, suspending agents, fillers, glidants, compression aids, binders or tablet-disintegrating agents or an encapsulating material. In powders, the excipient is a finely divided solid that is in admixture with the finely divided active ingredient. In tablets, the active ingredient is mixed with an excipient having the necessary compression properties in suitable proportions and compacted in the shape and size desired. The powders and tablets preferably contain up to 99% of the active ingredient. Suitable solid excipient includes, for example, calcium phosphate, magnesium stearate, talc, sugars, lactose, dextrin, starch, gelatin, cellulose, methyl cellulose, sodium carboxymethyl cellulose, polyvinylpyrrolidine and the like.

The anti-TDP-43 oligomer antibody of the present invention may also be formulated into liquid pharmaceutical compositions, which are sterile solutions or suspensions that can be administered by, for example, intravenous, intramuscular, subcutaneous, intrathecal, intraperitoneal, or intra-cerebella injection. Oral administration may be either liquid or solid composition form.

The medicament or said pharmaceutical compositions of this invention may also be formulated in a variety of dosage forms for mucosal application, such as buccal and/or sublingual drug dosage units for drug delivery through oral mucosal membranes. A wide variety of biodegradable polymeric excipients may be used that are pharmaceutically acceptable, provide both a suitable degree of adhesion and the desired drug release profile, and are compatible with the active agents to be administered and any other components that may be present in the buccal and/or sublingual drug dosage units. Generally, the polymeric excipient comprises hydrophilic polymers that adhere to the wet surface of the oral mucosa. Examples of polymeric excipients include, but are not limited to, acrylic acid polymers and copolymers; hydrolyzed polyvinylalcohol; polyethylene oxides; polyacrylates; vinyl polymers and copolymers; polyvinylpyrrolidone; dextran; guar gum; pectins; starches; and cellulosic polymers.

Accordingly, this invention also provides methods of treating mammals, preferably humans, of a TDP-43 oligomer associated disease, which comprises the administration of the medicament or said pharmaceutical composition of this invention that contains anti-TDP-43 oligomer antibody as described herein. Such medicament or composition is administered to a mammal, preferably human, by any route that may effectively transports the active ingredient(s) of the composition to the appropriate or desired site of action, such as oral, nasal, pulmonary, transdermal, such as passive or iontophoretic delivery, or parenteral, e.g., rectal, depot, subcutaneous, intravenous, intrathecal, intramuscular, intranasal, intra-cerebella, ophthalmic solution or an ointment. Further, the administration of the compound of this invention with other active ingredients may be concurrent or simultaneous.

In some embodiments, the effective dose administered to the subject is from about 1 to 100 mg/Kg body weight of the subject, such as about 10, 20, 30, 40, 50, 60, 70, 80, 90 or 100 mg/Kg body weight of the subject, preferably about 50 to 70 mg/Kg body weight of the subject, such as 50, 60 or 70 mg/Kg body weight of the subject; most preferably about 50 mg/Kg body weight of the subject. The dose can be administered in a single aliquot, or alternatively in more than one aliquot.

According to optional embodiments of the present disclosure, the method may further include the step of, administering to the subject an acetylcholinesterase inhibitor (AChEI), an Aβ inhibitor, or a muscarinic receptor agonist, either simultaneously or sequentially with the anti-TDP-43 oligomer antibody as described above.

In some embodiments, the AChEI is any of alantamine, cymserine, donepezil, ER 127528, galantamine, ganstigmine, huperzine A, phenserine, phenethylnorcymserine, rivastigmine, RS 1259, SPH 1371, tacrine, thiacymserine, or zanapezil. In other embodiments, the Aβ inhibitor is any of bapineuzumab, PTB2, scyllo-inositol, PPI 1019, RS 0406, SP 233, EGCG, Exberyl-1, or SEN 606. The muscarinic receptor agonist is oxotremorine or xanomeline.

The anti-TDP-43 oligomer antibody of the present invention may also be used as a tool for the detection or diagnosis of a TDP-43 oligomer associated disease in a subject. Accordingly, this invention provides a method for detecting or diagnosing a subject having or suspected of having a TDP-43 oligomer associated disease. The method includes steps of, obtaining a biological sample from the subject;

determining the amount of the TDP-43 oligomer in the biological sample by contacting the biological sample with an effective amount of the present antibody; and comparing the detected amount of the TDP-43 oligomer in the biological sample with that of a control sample obtained from a healthy subject; wherein a significantly higher or lower amount of the detected TDP-43 oligomer in the biological sample than that of the control sample indicates that the subject suffers from the TDP-43 oligomer associated disease.

The biological sample described herein includes, but is not limited to, a brain biopsy sample, a cerebrospinal fluid sample, a whole blood sample, a serum sample, a plasma sample, a urine sample, a mucus sample and purified or filtered forms thereof.

Antibody binding may be detected by techniques known in the art, such as radioimmunoassay, enzyme-linked immunosorbent assay (ELISA), "sandwich" immunoassay, in situ immunoassays (e.g., using colloidal gold, enzyme or radioisotope labels), western blot, agglutination assay (e.g., gel agglutination assay, hemagglutination assay and etc), complement fixation assay, immunofluorescence assay, and immunoelectrophoresis assay and etc. In one embodiment, antibody binding is detected by use of ELISA. In some embodiments, autoantibodies are detected in bodily fluids, including but are not limited to cerebrospinal fluid, whole blood, serum, plasma, mucus, and purified or filtered forms thereof. In one preferred example, antibodies were detected from a cerebrospinal fluid sample. In other embodiments, antibodies are detected from a brain biopsy sample.

To provide those skilled in the art tools to use the present invention, the anti-TDP-43 oligomer antibody of the invention is assembled into kits for the diagnosis, detection or confirmation of a neurodegenerative disease. In preferred embodiments, the presence of pathologic forms of TDP-43 reactive to the anti-TDP-43 oligomer antibody of this invention is used to provide prognosis to a subject. For example, the detection of a significant different level of pathologic forms of TDP-43 reactive to the anti-TDP-43 oligomer antibody of this invention, as compared to controls (derived from a healthy subject), in a biological sample is indicative of occurrence of the TDP-43 oligomer associated disease. The information provided is also used to direct the course of treatment. For example, if a subject is found to have pathologic forms of TDP-43, therapies for the treatment of the TDP-43 oligomer associated disease, such as AD, ALS and PD, may be started at an earlier time when they are more likely to be effective.

In one embodiment, the present invention provides a kit for the diagnosis of a TDP-43 oligomer associated disease by use of the anti-TDP-43 oligomer antibody of this invention. The components included in the kits are: a container, reagents for detecting TDP-43 oligomer in a biological sample, wherein the reagents comprise the anti-TDP-43 oligomer antibody of this invention prepared in accordance with the procedure described in one example of this invention; and a legend associated with the container and indicating how to use the anti-TDP-43 oligomer antibody of this invention for detecting the pathological form of TDP-43 (or TDP-43 oligomer as described herein) in the biological sample. The legend may be in a form of pamphlet, tape, CD, VCD or DVD. The kit may further comprise a negative control that indicates the normal level of the TDP-43 oligomer that forms a complex with the anti-TDP-43 oligomer antibody in a healthy subject.

The present invention will now be described more specifically with reference to the following embodiments, which are provided for the purpose of demonstration rather than limitation.

EXAMPLES

Materials and Methods.
Materials.
The isolated human TDP-43 from HEK cells was a gift from OriGene Technologies, Inc. (Rockville, Md., USA). Based on the product description, TDP-43 was obtained from transiently transfected human HEK 293 cells with a TrueORF clone, RC210639. The recombinant TDP-43 possessed a C-terminal Myc-DDK tag. The overexpressed recombinant TDP-43 protein was purified using an anti-DDK affinity column. The short-form of TDP-43 (residues 101-285) is prepared in accordance with procedures described by Kuo et al (Nucleic Acids Res (2009) 37, 1799-1808). Anti-N-terminal residues 1-260 TDP-43 antibody (denoted as $N_{1-260}$) for dot blotting and anti-TDP-43 antibody for immunohistochemistry were both purchased from Abcam (Cambridge, UK). Anti-C-terminal residues 350-414 TDP-43 antibody (denoted as $C_{350-414}$) was from Novus (Littleton, Colo., USA) and anti-amyloid oligomer antibody A11 was from BioSource (Invitrogen, Carlsbad, Calif., USA). Anti-DDK monoclonal antibody was from Origene Technologies, Inc. Aβ peptide was synthesized by peptide synthesis facility in the Genomics Research Center, Academia Sinica. Other chemicals were purchased either from Sigma Aldrich (St. Louis, Mo., USA) or Amresco (Solon, Ohio, USA). All cell culturing reagents were purchased from Gibco (Invitrogen) except for further indication.

Purification of TDP-43.
The N-terminal His-Tag TDP-43 was cloned from the plasmid pCMV-Taq2B containing the cDNA encoding full-length TDP-43. The amplified product was double digested with XhoI/BamHI and subcloned into pET14b vector (Novagen, Merck KGaA, Darmstadt, Germany) to generate an N-terminal His-tag. The N-terminal His-tagged TDP-43 was transformed and overexpressed in E. coli strain Rosetta 2. (Novagen, Merck KGaA, Darmstadt, Germany). The cells were harvested and lysed by a microfluidizer on ice in 30 mM Tris-HCl buffer, pH 8, containing 500 mM NaCl, 10% glycerol, 1 mM DTT, 2% RNase A, 2% DNase I, and protease inhibitor cocktail (Complete, EDTA-free, Roche Applied Science, Mannheim, Germany). The lysate was centrifuged at 27,000×g, 4° C. The supernatant was loaded onto Ni-NTA affinity column (GE healthcare Bio-Sciences AB, Uppsala, Sweden) equilibrated in a buffer containing 30 mM Tris, pH 8, 500 mM NaCl, 1 mM DTT, 20 mM imidazole, and 10% glycerol. Imidazole step gradients in the same running buffer were performed. TDP-43 was eluted at approximately 200 mM imidazole. Purified his-tagged TDP-43 protein was run on SDS-PAGE and identified by Coomassie blue staining. The recombinant TDP-43 contained extra N-terminal residues MGSSHHHHHHSSGLVPRGSHMLE. The calculated molecular mass is 47,147 Da. The protein was further dialyzed as indicated. Protein concentration was quantified after background subtraction by absorption at 280 nm with the extinction coefficient of 44,920 $cm^{-1}M^{-1}$ according to the equation described by Nick Pace (Pace et al., (1995) Protein Sci 4, 2411-2423). For the short-form of TDP-43, the extinction coefficient of 15,470 $cm^{-1}M^{-1}$ was used.

Size exclusion chromatography (SEC).

Superdex-200 10/300 GL analytical gel-filtration column (GE healthcare Bio-Sciences AB, Uppsala, Sweden) was standardized by molecular weight markers, ferritin (440 kDa), β-amylase (200 kDa), bovine serum albumin (66 kDa), cytochrome C (12.4 kDa) in the running buffer containing 30 mM Tris, pH 7.4, 150 mM NaCl. The flow rate was 0.5 ml/min. A volume of 300 µl of the recombinant TDP-43 from E. coli filtered by 0.2 µm filter membrane was injected into the Superdex-200 column. One ml fractions were collected automatically by a fraction collector. The preload sample and the oligomer fraction were collected and subjected to dot blotting probed by A11 (1:1000) with different exposure times due to much diluted signal from the oligomer fraction. The oligomer fraction was characterized with dynamic light scattering. A volume of 100 µl of TDP-43 obtained from HEK cells at 2 µM were also examined with the same procedure. The fractions were analyzed by slot blotting.

Slot Blotting.

Fractions of the size-exclusion chromatography of TDP-43 isolated from HEK293 cells were examined by slot blotting because of their low concentration. A 200 µl aliquot of every 1 ml fraction was loaded onto a Bio-Dot SF microfiltration apparatus (Bio-Rad, Hercules, Calif., USA) equipped with an in-house vacuum system. Anti-DDK monoclonal antibody (OriGene Technologies, Inc., Rockville, Md., USA) was used as primary antibody for the detection. Intensity was quantified by Image J 1.42 (National Institutes of Health, MD, USA).

Dot Blotting.

Purified TDP-43 was diluted 10 times into 10 mM Tris-HCl buffer, pH 8, with or without denaturants. Each sample in different conditions contains either no denaturant, 9 M urea, 7.2 M GdnHCl, or 2% SDS. The final TDP-43 concentration was 0.4 µM. The samples were either incubated for 1 hr at the room temperature or 90° C. The TDP-43 samples, 2 µl, were dotted onto nitrocellulose membranes and were subjected to dot blotting. Briefly, after blocking and washing with Tris-buffered saline containing 0.002% Tween 20 (TBST), the membranes were subjected to anti-N-terminal residues 1-260 TDP-43 antibody (1:2,000), Anti-C-terminal residues 350-414 TDP-43 antibody (1:2,000), and anti-amyloid oligomer antibody, A11, (1:1,000) in 5% milk with TBST followed by the corresponding horseradish peroxidase-conjugated secondary antibodies anti-rabbit or anti-mouse IgG (1:5,000; Millipore, Billerica, Mass., USA). The membranes were developed with ECL chemiluminescence reagent (Millipore).

Transmission Electron Microscopy.

Freshly purified TDP-43 was dialyzed into a buffer containing 10 mM Tris, pH 8, at 4° C. overnight. The sample was centrifuged at 17,000×g, 4° C., for 30 min to remove precipitates and the supernatant was quantified and subjected to TEM imaging. The TDP-43 samples were placed on glow-discharged, 400-mesh Formvar carbon-coated copper grids (EMS Inc., Hatfield, Pa., USA) for 5 min, rinsed, and negatively stained with 2% uranyl acetate. The samples were examined with Tecnai G2 Spirit TWIN TEM (FEI, Hillsboro, Oreg., USA) or Hitachi H-7000 TEM (Hitachi Inc., Japan) with an accelerating voltage of 75 kV.

Atomic Force Microscopy.

Freshly purified TDP-43 was dialyzed into a buffer containing 10 mM Tris, pH 8, at 4° C. overnight. The sample was centrifuged at 17,000×g, 4° C., for 30 min to remove precipitates and the supernatant was quantified and subjected to AFM imaging. A volume of 10 µL TDP-43 was dropped onto freshly sliced mica (Ted Pella, Redding, Calif., U.S.A.) and incubated for 5 min for sample adhesion. The sample was washed by 1 ml ddH$_2$O and gently removed from the top of the tilted mica. The sample was left to dry in the room temperature and subjected to AFM imaging (Nanonics, Jerusalem, Israel) using tapping mode. AFM tips, PPP-ZEILR (Nanosensors, Neuchatel, Switzerland) with a spring constant of 1.6 N/m and the tip radius <10 nm were employed for the experiment.

Dynamic Light Scattering.

The eluted oligomer fraction from SEC was used for dynamic light scattering. The sample was in a buffer containing 30 mM Tris, pH 7.4, and 150 mM NaCl. Data were obtained with a Zetasizer Nano ZS dynamic light scattering instrument (Malvern Instruments, Worcestershire, UK) equipped with 50 mW later fiber. Appropriate parameters of viscosity and refractive index were set for each solution and the temperature was kept at 25° C.

Circular Dichroism.

Freshly purified TDP-43 was dialyzed into a buffer containing 10 mM Tris, pH 8, at 4° C. overnight. The sample was centrifuged at 17,000×g, 4° C., for 30 min to remove precipitates and the supernatant was quantified and subjected to CD measurement. Far-UV CD spectra were measured in a circular quartz cell (Hellma, Forest Hills, N.Y., USA) by Jasco J-815 spectropolarimeter (Jasco Inc., Easton, Md., USA) with 1 mm path length at room temperature. The spectra were collected from 250 to 190 nm and corrected with buffer background.

Intrinsic and Bis-ANS Fluorescence Spectroscopy.

Freshly purified TDP-43 was dialyzed into a buffer containing 10 mM Tris, pH 8, at 4° C. overnight. The sample was centrifuged at 17,000×g, 4° C., for 30 min to remove precipitates and the supernatant was quantified. The intrinsic fluorescence of TDP-43, at 1.5 µM, was collected from 305 to 400 nm while excitation at 280 or 295 nm. The Bis-ANS spectra of TDP-43, TDP-43s, and buffer control were collected from 450 to 600 nm with excitation at 400 nm. The samples contain 0.8 µM TDP-43 and 5 µM Bis-ANS. All experiments were done at 25° C. with a circulating water bath using FluoroMax-3 spectrofluorometer (Horiba Jobin Yvon, Kyoto, Japan).

Thioflavin T Binding.

Freshly purified TDP-43 was dialyzed into a buffer containing 10 mM Tris, pH 8, at 4° C. overnight. The sample was centrifuged at 17,000×g, at 4° C., for 30 min to remove precipitates and the supernatant was quantified. The TDP-43 sample and Aβ40 fibrils were used to detect thioflavin T binding. The samples, 1 µM, were mixed with equimolar thioflavin T and excited at 442 nm, and the emission spectra from 455 to 505 nm were collected. Aβ40 fibril stock, 25 µM, was prepared as previously described (Chen and Glabe, J. Biol. Chem. (2006) 281, 24414-24422). Briefly, synthetic Aβ was dissolved in 6 M GdnHCl and refolded to 10 mM phosphate buffer, pH 7.4. Then Aβ, 25 µM, was incubated at 25° C. in quiescence for more than 10 days. The mature fibrils were then diluted to 1 µM prior to the experiments. The spectra were subtracted from the buffer background.

Congo Red Spectroscopy.

Absorbance of dialyzed TDP-43 and mature Aβ fibrils, 0.5 µM, was measured from 400 nm to 600 nm in the presence of f 10 µM Congo Red by a UV/vis spectrophotometer DU800 (Beckman Coulter, Calif.).

Dot Blotting by OC Antibody.

The dialyzed TDP-43 and Aβ fibrils (2 µl, 0.5 µM) were dotted onto nitrocellulose membranes and standard dot blot procedure was performed. OC antibody (Millipore, 1:10,000) and HRP-conjugated anti-rabbit IgG (1:10,000) were employed.

Fluorescence Titration for DNA Binding.

Fluorescence titration was employed to monitor protein conformational changes upon DNA binding. Freshly purified and dialyzed full-length TDP-43 and short-form of TDP-43 (residues 101-285), at 1.5 µM, in 30 mM Tris-HCl, pH 8, were titrated with single strand TAR DNAs including TAR DNA A-site (SEQ ID NO: 9) and B-site (SEQ ID NO: 10). The intrinsic protein fluorescence was excited at 280 nm to monitor the conformational change of TDP-43. The emission spectra were collected by FluoroMax-3 spectrofluorometer (Horiba Jobin Yvon, NJ, USA). The emission maxima at 350 nm for full-length or short-form TDP-43 were collected, subtracted with the DNA controls, and corrected with the dilution factor. Then, the data were normalized to the starting intensity and further fitted to a single protein and ligand binding equation (Chen et al., Protein Sci (2004) 13, 2196-2206):

$$P+L \leftrightarrow PL$$

$$r=(2Pt)^{-1}*[(Kd+Lt+Pt)-((Kd+Lt+Pt)^2-4PtLt)^{1/2}]$$

where γ is the fraction of the observed signal changes representing the bound protein fraction, $P_t$ is the total TDP-43 concentration, $L_t$ is the total ligand concentration, and Kd is the dissociation constant. The data and fits are plotted against the ratio of DNA and TDP-43.

Oligomer Cross-Seeding and ThT Assay.

Aβ was prepared following our previous protocol (Chen et al., J. Biol. Chem. (2011) 286, 9646-9656; Ni et al., FASEB (2011) 25, 1390-1401). Aβ40 was dissolved in buffer A (10 mM sodium phosphate, pH 7.4) containing 8 M GdnHCl, refolded, and quantified using absorption at 280 nm (ε=1,280 cm$^{-1}$M$^{-1}$). The experimental samples containing 25 µM Aβ, 50 µM ThT, and different concentrations of freshly dialyzed TDP-43 ranging from 0 to 1 µM (0-4%) were prepared in 10 mM Tris-HCl, pH 8, and 150 mM NaCl. The samples were then incubated in a 96-well ELISA plate in quiescence, sealed with a transparent film, and monitored by a microplate reader (SpectraMax M5, Molecule Devices) at 25° C. at various times. ThT emission was measured at 485 nm while excitation was at 442 nm.

Photo-Induced Cross-Linking (PICUP).

The experiment was performed as described previously (Bitan et al., J. Biol. Chem. (2001) 276, 35176-35184). Briefly, the Aβ stock was prepared by use of a buffer containing 8 M urea and 10 mM sodium phosphate, pH 7.4, to facilitate running on SDS-PAGE. Aβ samples at 25 µM were prepared in a buffer containing 10 mM Tris-HCl, pH 8, and 150 mM NaCl with or without TDP-43 at different concentrations as indicated. The samples were immediately subjected to PICUP assay. A 90% Aβ solution was mixed with 5% each of 3 mM Ru(Bpy) and 20 mM APS. After mixing, samples were exposed to a blue-light LED in a closed chamber with a manual switch for 30 s. The cross-linking reaction was stopped by adding the SDS-PAGE sample buffer, and the samples were run on 16% Tris-tricine SDS-PAGE. All actions were performed without delay. The gel was subjected to Western blotting with anti-Aβ antibody 6E10 (Chemicon Inc., Billerica, Mass.) recognizing Aβ residues 1-17 and anti-N-terminal TDP-43 1-260 antibody.

Cytotoxicity of TDP-43 Using Human Neuroblastoma.

To perform cytotoxicity of TDP-43, MTT (3-[4,5-Dimethylthiazol-2-yl]-2,5-diphenyl-tetrazolium bromide) and lactate dehydrogenase (LDH) (Promega, Madison, Wis., United States) assays were first employed using human neuroblastoma BE(2)-C cells (ATCC number CRL-2268). The cells were cultured in RPMI growth medium (Gibco) with 10% fetal bovine serum (FBS; Biological Industry) at 37° C. under 5% CO$_2$ and humidified atmosphere. A total of 60,000 cells per well was seeded in transparent 96-well ELISA plate (Corning, N.Y., USA) and incubated overnight. The cells were then washed and replaced by 40 µl of serum-free RPMI media followed by addition of 10 µl serially diluted TDP-43 samples with the dialysis buffer. The TDP-43 samples were freshly dialyzed and centrifuged. The supernatant was employed and the dialysis buffer served as a buffer control. The cells were further incubated for 24 hr, and MTT assay was performed following the standard protocol. In brief, a volume of 7 µl of 5 mg/ml MTT was added in each well and cells were incubated for 3 hr. Then, the media were discarded and DMSO was added to lyze the cells until the purple formazan crystals were fully dissolved. Absorbance at 570 and 690 nm were measured by an ELISA plate reader (SpectraMax M5, Molecule Devices, USA) and the signals at 570 nm were subtracted from that of 690 nm. The data obtained from five replicas were averaged and corrected with the sample background without cells. The cell viability was shown after normalization of the data using the cell treated with buffer as 100%. LDH assay was performed following the manufacturer's protocol. Briefly, a number of 20,000 cells was seeded in the growth medium and incubated for 24 hr. The samples were treated as described in MTT assay. LDH substrate was mixed with the assay buffer and kept at room temperature. The cells were cooled to room temperature for 30 min before substrate addition. After 1 hr of dark incubation, the substrate fluorescence was excited at 560 nm and emission at 590 nm was measured by the ELISA plate reader. The data were obtained from three replicas, averaged, and corrected by the sample background without cells. The p-values of MTT and LDH assays were calculated using unpaired Student's t-test.

Cytotoxicity of TDP-43 Using Mouse Primary Cortical Neurons.

The pregnant C57BL/6JNarl mice were purchased from National Laboratory Animal Center (NLAC, Taiwan) with the approval of the Institutional Animal Care and Use Committee (IACUC) at National Yang Ming University, Taipei, Taiwan. Primary cortical neuronal cultures, were generated from embryonic day 19 mice and were seeded in 96-well plates (2×10$^5$ cells/well) with neurobasal medium (21103049, GIBCO, USA) containing 2 µM FdU. After growing 8 days in vitro, primary neuronal culture were treated with freshly dialyzed soluble TDP-43 for 24 hr, and then incubated with 0.5 mg/ml MTT for 3 h. The dialysis buffer was served as buffer control. MTT formazan crystals were then dissolved by equal volume of lysis buffer containing 10% SDS and 20 mM HCl overnight. The absorbance at wavelength 570 nm in each well was measured on an ELISA plate reader (TECAN, Switzerland). The data were obtained from three replicas, averaged, and corrected by the sample background without cells. The p-values for MTT assay were calculated using unpaired Student's t-test.

Immunocytochemistry.

Primary neuron cells were cultured on 24-well plates with 12 mm glass coverslips (3×10$^5$ cells/well), and each well was coated with poly-D-lysine. Cells were treated with TDP-43 (0.6 µM) or buffer control for 24 hr at 37° C. in a humidified atmosphere with 5% CO2, and were fixed by 4% paraformaldehyde for 20 min at room temperature. Then, the cells were washed with PBS 10 min for 3 times, and blocked with blocking buffer (PBS containing 0.3% triton x-100 and 10% FBS) for 1 hr at room temperature. After blocking, cells were first hybridized by the primary antibodies of microtubule associated protein-2 (MAP-2) (MAB378, Millipore, USA) and polyclonal rabbit anti-glial fibrillary acidic protein (GFAP) (Z0334, DAKO, Glostrup, Denmark) for 2 hr at room temperature and then hybridized by the fluorescent dye conjugated secondary antibodies of Texas-Red-conjugated goat anti-mouse IgG (AbD Serotec, UK) or FITC-conjugated goat anti-rabbit IgG (Millipore, USA) for 1 hr at room temperature. Finally, cells were mounted by mounting gel containing DAPI (VECTASHIELD®+DAPI, H-1200, Vector Lab.) and observed by Olympus fluorescence microscope (BX-61, Olympus).

Intrahippocampal Injection of TDP-43.

Two-month-old male C57/BL6J mice were applied to intrahippocampal injection that purchased and bred in animal center of National Cheng Kung University (NCKU) (Tainan, Taiwan) following the guidelines of IACUC of NCKU. Animals were anesthetized with isoflurane inhalation (1.2% in oxygen) via a nose tube. Each animal received bilateral intrahippocamal injection of recombinant full-length TDP-43. The stereotaxic coordinates were in relation to bregma as follows: anteroposterior (AP), −2 mm; mediolateral (ML), ±1 mm; dorsoventral (DV), −2 mm. The injection needle slowly approached to the desired depth and 2 µl TDP-43, 2.2 µM, was injected using a stainless-steel syringe needle (33-gauge) connected to a microsyringe (Hamilton Company, NV, USA) at an injection rate of 1 µl/min. The needle was left in place for an additional 5 min to limit the diffusion of the injected TDP-43.

Immunofluorescent Staining of the Mouse Brains.

Twelve-month-old male wild type mice, and 6- and 12-month-old TDP-43 Tg$^{+/+}$ transgenic mice were adopt for immunofluorescent staining. All mice were also cared in animal center of NCKU following the guidelines of IACUC of NCKU. Two weeks after TDP-43 injection, the adult mice were deeply anesthetized and perfused transcardially with 4% paraformaldehyde (PFA)/0.01M phosphate buffered saline (PBS), pH 7.4. The brain was removed and then stored in 30% sucrose/4% PFA solution overnight. 10-µm-thick sections were treated with a blocking solution containing 0.2% Triton X-100 and 5% normal donkey serum in 0.01 M PBS at room temperature for 1 h. For the experiments of intrahippocampal injection, the sections were incubated in mouse monoclonal anti-NeuN (1:300, Millipore, Temecula, Calif.) at 4° C. overnight and Alexa Fluor 555-conjugated donkey anti-mouse antibody (1:300, Chemicon, Temecula, Calif.) at room temperature for 1 h. The sections were then counterstained with DAPI and mounted with fluorescent mounting medium (DAKO, Glostrup, Denmark). All sections were examined under an upright fluorescent microscope (BX51, Olympus, Tokyo, Japan). For the colocalization study in transgenic mice, the sections were incubated with anti-TDP-43 antibody (1:1000, Abcam, ab104223), TDPO (1:1000, LTK BioLaboratories, Taiwan), Alexa Fluor 488-conjugated goat anti-rabbit antibodies and the Alex Fluor 555-conjugated donkey anti-mouse antibodies (1:300, Invitrogen). The sections were then incubated with DAPI and coverslipped with fluorescent mounting medium (fluorescent mounting medium; Dako). All sections were examined in a laser scanning confocal microscope (Nikon TE2000EPFS-C1-Si).

TDP-43 Oligomer-Specific Polyclonal Antibody Production and Characterization.

The purified full-length TDP-43 was dialyzed into 10 mM Tris-HCl, pH 8.0, at 4° C., and concentrated to approximately 0.2 mg/ml to serve as immunogen. New Zealand white rabbits were immunized with the immunogen following the standard protocol for polyclonal antibody production (LTK BioLaboratories, Taiwan). Briefly, the immunogen was injected 0.5 ml into the rabbit at 2-week intervals. After 6 injections, the rabbit was sacrificed, and the blood serum was obtained for usage. For characterization of TDP-O by dot blotting and ELISA, full-length TDP-43 was subjected to SEC (Superdex-200 10/300 GL, GE healthcare Bio-Sciences AB, Uppsala, Sweden) in a buffer containing 30 mM Tris-HCl, pH 8.0, and 150 mM NaCl with a flow rate of 0.3 ml/min. One ml fractions were collected and subjected to dot blotting probed by TDP-O and $N_{1-260}$ antibodies. The TDP-43 oligomer and monomer fractions were further quantified by Micro BCA™ Protein Assay Kit (Thermo Scientific, Rockford, Ill.) and coated onto ELISA plate with serial dilution. ELISA following the standard protocol was performed. Briefly, the coated samples were incubated overnight at 4° C., then blocked for 2 hr at room temperature with 10% skim milk in TBST. The plates were washed and probed by TDP-O (1:12,500 in 3% skim milk in TBST) or anti-N-terminal residues 1-260 TDP-43 antibody (1: 1,000 dilution in 3% skim milk in TBST) for 2 hr at room temperature. After washing, the plates were subjected to anti-rabbit horseradish peroxidase-conjugated secondary antibodies (1:1,000; Merck Millipore, Billerica, Mass., USA) for 2 hr at room temperature, washed, then developed by 100 µl 3,3,5,5-tetramethylbenzidine (TMB, Merck Millipore, Billerica, Mass., USA). The reaction was stopped with addition of 100 µl of 250 mM HCl and the absorbance was read at 450 nm by SpectraMax M5 (Molecular Device, Sunnyvale, Calif.).

Generation of β5 Fibrils.

β5 peptide within RRM2 domain of TDP-43 fragment was chemically synthesized (MDBio, Inc., USA). The peptide was solubilized by acetonitrile and diluted 10 times with PBS buffer (pH 7.4) at 5 mg/ml. The supernatant was collected after centrifugation at 17,000×g for 30 min and filtered through a 0.2 µm filter membrane (Pall, USA). Then, the sample was incubated in quiescence at room temperature for 7 days. β5 fibrils were formed and the morphology was observed by TEM. The sample was subjected to dot blotting probed by TDP-O antibody following the aforementioned procedure.

TDP-O Staining of the Brain Tissues of FTLD-TDP Patients.

Paraffin-embedded tissue sections were de-waxed with three washes of Xylene. Tissues were then hydrated through an alcohol gradient, followed by a five-min wash in 1×TBS. Antigen recovery was performed using 10 mM sodium citrate (pH 6) by microwaving for 15 min at full power (1,500 watts). Endogenous peroxidase activity was blocked by incubating the tissue in 3% hydrogen peroxide in 1×TBS for 20 min, followed by a five-min wash in 1×TBS. Non-specific binding was blocked by incubating the tissues in 10% normal goat serum (Invitrogen) for 1 hr at ambient temperature. Primary antibody was diluted at 1:1000 in antibody buffer (1×TBS supplemented with 5% bovine serum albumin and 0.5% Tween-20) and applied to the tissues overnight at 4° C. Slides were washed three times in wash buffer (1×TBS/0.5% Tween-20). Biotinylated secondary antibodies were applied at 1:500 dilution in antibody buffer for 1 hr at ambient temperature. Tissue was washed three times in wash buffer, then incubated with Vectastain ABC peroxidase reagent (Vector Labs, PK-6100) for 30 minutes, followed by one wash in 1×TBS. The tissues were then exposed to DAB peroxidase substrate reagent (Vector Labs, SK-4100) for 2-10 min to achieve optimal staining.

Tissues were counterstained with Mayers Hematoxylin Solution (Sigma Aldrich), and then dehydrated through an alcohol gradient followed by a xylene wash. Tissue slides were mounted using Permount (Sigma Aldrich). Post-mortem brain samples from three control, three FTLD-TDP, and three AD patients were provided by the Alzheimer's Disease Center at University of California Davis. The study was approved by the Institutional Review Board. Informed consent to share research tissue after death was obtained from all patients.

IP and Immunolabeling of TDP-43 Oligomers in FTLD-TDP Brain.

The frozen brain tissues of two control and one FTLD-TDP patient were lysed at ~0.05 g/ml with a lysis buffer containing 50 mM Tris, pH 7.4, 150 mM NaCl, 0.5% Triton X-100, and protease inhibitor cocktail (Calbiochem, Merck Millipore). The lysed samples were homogenized on ice by a tissue grinder (Wheaton, N.J., USA). After homogenization, the soluble fractions were collected after centrifugation at 17,000×g for 10 min at 4° C. and saved for IP analysis. Prior to tissue fractioning, crossed-linked TDP-O antibodies on the IP beads were prepared following the manufacturer's procedure. Briefly, a total of 40 μg of TDP-O antibody was incubated with 10 μl each of protein A and G Mag Sepharose™ Xtra (GE healthcare) in the binding buffer (50 mM Tris pH 7.5, 150 mM NaCl) at room temperature for 1 hr. After antibody binding on the beads, crosslinking was performed by crosslink reagent (50 mM dimethyl pimelimidate dihydrochloride and 200 mM triethanlamine, pH 8.9) at RT for 1 hr and the reaction was stopped by the addition of 100 mM ethanolamine, pH 8.9, at RT for 30 min. Next, the soluble fractions of hippocampus were incubated with the TDP-O antibody-crosslinked IP beads at room temperature for 1 hr. The unbound species were removed by at least 6 washes with the binding buffer. The targeted protein was eluted by Gentle Ag/Ab Elution Buffer (Thermo), pH 6.6, and the eluent was saved for EM imaging and immunogold labeling. For immunogold labeling, 10 μl of eluent was placed on 400-mesh Formvar carbon-coated copper grids (EMS Inc., Hatfield, Pa., USA) for 5 min, washed by PBS, and then blocked by 1% BSA in PBS solution at RT for 1 hr. After blocking, the grids were labeled by $N_{1-260}$ antibody (1:5,000, ab57105, Abcam) in 0.1% BSA containing PBS solution at RT for 1 hr, and washed by high salt tween (HST) buffer (50 mM Tris, pH 7.5, 500 mM NaCl, and 0.1% Tween-20) and PBS. After washing, grids were incubated with 6 nm gold-conjugated secondary anti-mouse IgG antibody (1:40, Jackson ImmunoResearch) at RT for 1 hr. The unbound antibody was removed by HST and PBS washes. Then, the grids were fixed by 1% glutaraldehyde containing PBS at RT for 10 min and washed 6 times by ddH$_2$O. Finally, the grids were rinsed, negatively stained with 2% uranyl acetate, and subjected to TEM imaging with FEI Tecnai G2 F20 S-TWIN TEM.

Purification of Monoclonal TDP-O Antibodies.

The monoclonal TDP-O antibodies were purified by protein G agarose kit (KPL) following the manufacturer's procedure. Briefly, Protein G agarose (1.5 ml) supplied in 20% ethanol was poured into a disposable column. The resin was washed with 10 ml wash buffer (0.1 M sodium phosphate, pH 7.4, 0.15 M NaCl). Conditional medium of TDP-O hybridoma cells (5 ml) was diluted with 5 ml binding buffer. Then, the mixed sample solution was loaded into the column and the column was inverted for mixing. Then, the column was washed by 5 ml wash buffer for 4 times until OD 280 nm was close to 0. The antibody was then eluted gently by adding 1 ml elution buffer (0.2 M glycine, pH 2.85) and collected in a collection tube that contained 240 μl 5× wash buffer. The antibody was concentrated, and the buffer was exchanged to wash buffer by Amicon Ultra-4 30 kDa cutoff (Millipore). The concentration of the antibody was quantified by absorbance at 280 nm (absorbance of 1 mg antibody=1.34).

Indirect ELISA.

ELISA 96-well plates (Nunc MaxiSorp) were coated with 20 ng full-length TDP-43 oligomer protein dissolved in 200 μl in TBS (50 mM Tris, pH 7.4, 150 mM NaCl) at 4° C. overnight. After removing the coating solution, TBS buffer with and without 0.2% SDS were added into the coated wells at room temperature for 1 hr. TDP-43 oligomers treated with SDS will denature, whereas, TDP-43 oligomers treated without SDS will maintain the oligomer conformation. After treatment, the buffer was removed and the wells were blocked with 200 μl 10% skim milk in TBST buffer (20 mM Tris, pH 7.6, 137 mM NaCl, 0.001% Tween 20) for 2 hr at room temperature. After washing three times with PBST (300 μl/well), 100 μl of diluted mTDP-O antibodies (from 0.00001 to 2 μg/ml) in TBST containing 5% skim milk was added and incubated for 1 hr at room temperature. After washing 2 times with 300 μl PBS, the bound antibodies were detected by using the following 100 μl HRP conjugated anti-mouse antibody (1:1,000) diluted in 5% skim milk in TBST. After incubation for 1 hr at room temperature and washing twice by 300 μl PBS, 3, 3', 5, 5'-tetramethylbenzidine (KPL SureBlue) (100 μl) was added to each well and the mixture was incubated for 10 min at room temperature. The reaction was stopped by adding 100 μl 250 mM HCl to the mixture, and the optical density at 450 nm was measured by SpectraMax M5 (Molecular Devices).

Preparation of TDP-43 Oligomers and Monomers for Indirect ELISA Assay.

TDP-43 protein (180 μg/ml) was concentrated from 3 to 1 ml by using Amicon Ultra-4 30 kDa cutoff. Concentrated TDP-43 protein solution, 500 μl, was loaded onto a Superdex 200 10/300 GL column and eluted with 30 mM Tris, pH 8.0, 50 mM NaCl at a flow rate of 0.3 ml/min. Fractions (500 μl per fraction) were collected and the fractions containing TDP-43 oligomers or monomers were pooled separately. The protein concentration was quantified by micro BCA assay (Thermo). TDP-43 monomers or oligomers (300 ng) were coated on 96-well ELISA plates (Nunc MaxiSorp). Conditional medium of TDP-O hybridoma cell (100 μl) (1:1,000) were used to detect TDP-43 oligomers by indirect ELISA assay as mentioned above.

Determination of Antibody Isotypes.

The isotyping of mTDP-O antibody was performed by an ELISA mouse monoclonal antibody (mAb) isotyping Kit (Thermo) following the manufacturer's procedure. In this assay, ELISA strip-well plates with individual wells pre-coated with anti-mouse heavy-chain capture antibody (anti-$IgG_1$, $IgG_{2a}$, $IgG_{2b}$, $IgG_3$, IgA and IgM) or anti-mouse light-chain capture antibody (kappa or lambda) were used. Briefly, the conditional medium of TDP-O hybridoma cell lines were diluted in 50 fold in TBS and the samples were added to each well of the 8-well strip. Then, the HRP conjugated anti-mouse IgG+IgA+IgM (50 μl) was added to each well of the 8-well strip and the reaction was incubated for an hr at room temperature. After 3 times washing, TMB substrate (75 μl) was added to each well and the plate was incubated at room temperature in dark for 10 min. Next, the reaction was stopped by adding 75 μl of 0.18 M sulfuric to acid. The absorbance of each well was read by SpectraMax M5 (Molecular Devices) at 450 nm.

Cloning and Sequencing the Ig Variable (V) Genes.

Total RNA was prepared from 2×10$^6$ hybridoma cells using GeneJET RNA purification kit (Thermo). cDNA synthesis was synthesized by using Maxima First Strand cDNA synthesis kit (Thermo). Then, mouse Ig-Primer Sets (Novagen) and GoTaq® G2 Green Master Mix (Promega) were used to amplified Ig heavy and kappa genes. The PCR products were cloned by TOPO® TA Cloning® Kit (Invitrogen). Finally, DNA sequencing was performed by Mission Biotech.

Cytotoxicity Assay.

MTT assay was employed to examine the inhibitory effect of monoclonal TDP-O antibody on TDP-43 oligomers-induced cytotoxicity. Human neuroblastoma BE(2)-C cells (ATCC #CRL-2268) were incubated at 37° C. under 5% $CO_2$ and cultured in RPMI media with 10% fetal bovine serum. Cells were seeded in RPMI media in a 96-well plate with 40,000 cells per well and incubated for 24 hr. Monoclonal TDP-O-3 (5 mg/ml) was prepared without further dilution, or with 2- or 4-folds dilution with Dulbecco's PBS. The media were discarded, and the cells were washed once by RPMI media without FBS. RPMI media (40 µl) were added to each well followed by the addition of 20 µl of 1.5 µM TDP-43 oligomers and 1 µl of 5, 2.5, or 1.25 mg/ml TDP-O antibody solution. The cells were incubated for an additional 24 hr. Afterwards, 7 µl of 5 mg/ml MTT solution was added and incubated for 3 hr. The media were discarded, and DMSO was used to lyse the formazan crystals. Absorbance at 570 and 690 nm was measured by an ELISA microplate reader SpectraMax M5 (Molecular Devices). The absorbance differences between 570 and 690 nm were calculated, averaged (n=3), and obtained by subtracting the background without cells. Each data set was normalized using the buffer control. Statistical analysis was performed by one-way ANOVAs.

Example 1 Full-Length TDP-43 Readily Forms Aggregates

In this example, the mechanism of TDP-43 pathology was investigated.

Figure 1B:
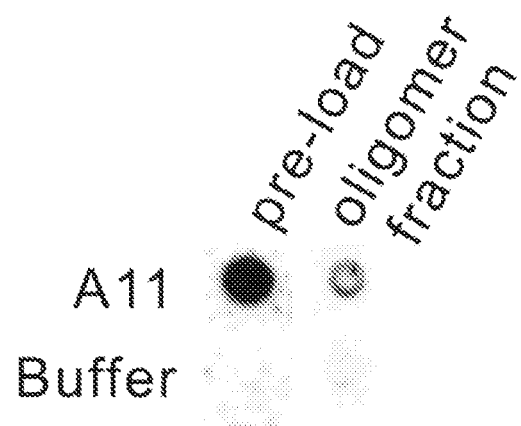

A recombinant full-length human TDP-43 in *E. coli* (TDP-43 with N-terminal His-Tag, MW 47,145 Da) and a TDP-43 protein purified from HEK293 cells were respectively obtained in accordance with the procedures described in "Materials and Methods." The thus obtained TDP-43 proteins were then subject to SEC analysis, and results are depicted in FIG. 1A. As evidenced in FIG. 1A, more than 86% of TDP-43 was eluted in the void volume, and slot blotting confirmed the majority of the recombinant full-length TDP-43 proteins from two different sources readily formed large aggregates. Since TDP proteinopathies are characterized by inclusion body (IB) formation and high-molecular-weight aggregates were found in the recombinant full-length TDP-43, we speculated that TDP-43 may form oligomers resembling the amyloid oligomers in amyloidosis. Therefore, the conformation-dependent anti-amyloid oligomer-specific antibody, A11, generated against Aβ oligomer mimics, was used to examine the TDP-43 oligomers, and we found both TDP-43 samples, but not the corresponding buffers, were immunoreactive with A11 (FIG. 1B). The oligomer fraction containing diluted TDP-43 exhibited weaker intensity.

Figure 1C:
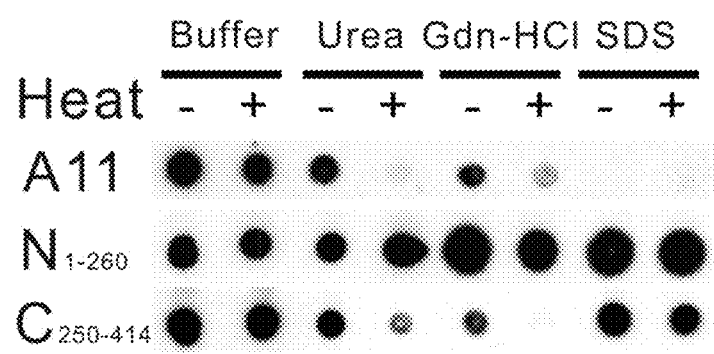

To confirm whether the recognition is conformation-dependent, different denaturing methods were employed to destruct TDP-43 oligomers before subjecting them to dot blotting by A11 as well as anti-N-terminal and C-terminal TDP-43 antibodies (FIG. 1C). The protein was incubated in various buffers, namely, with or without 9 M urea, 7.2 M GdnHCl, or 2% SDS, and further treated at 90° C. for 1 h. For A11 detection, heating did not significantly alter the detection signal in the native buffer. However, the signals were weakened in the presence of high concentrations of urea or GdnHCl and were nearly abolished by additional heat treatment. The signals were not detected in the presence of 2% SDS, regardless of heating. By contrast, the anti-N-terminal antibody recognized TDP-43 consistently across all conditions, confirming that equal amounts of proteins were dotted. The recognition by the anti-C-terminal antibody was diminished or completely lost when the samples were denatured in urea and heating or when the samples were denatured in GdnHCl, with or without heating. These findings indicate that the epitope recognized by the anti-C-terminal TDP-43 antibody is altered in these denaturing conditions.

Taken together, the results indicated that the recombinant full-length TDP-43 readily forms high-molecular-weight species, which share a common epitope with amyloid oligomers. These species are highly stable under chemical denaturation but are SDS-sensitive.

Example 2 Full-Length TDP-43 Forms Heterogeneous Spherical Oligomers

Figure 1D:
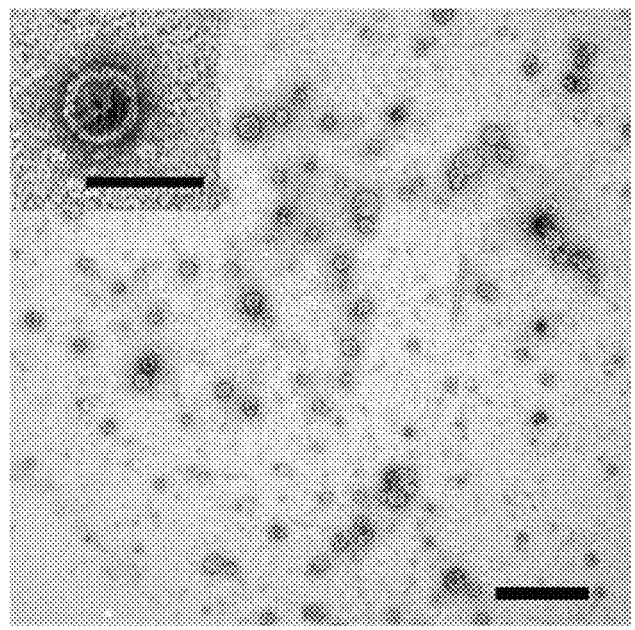
Figure 1E:
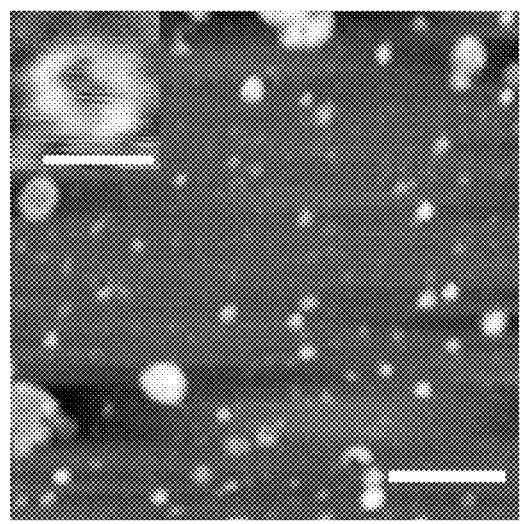
Figure 1F:
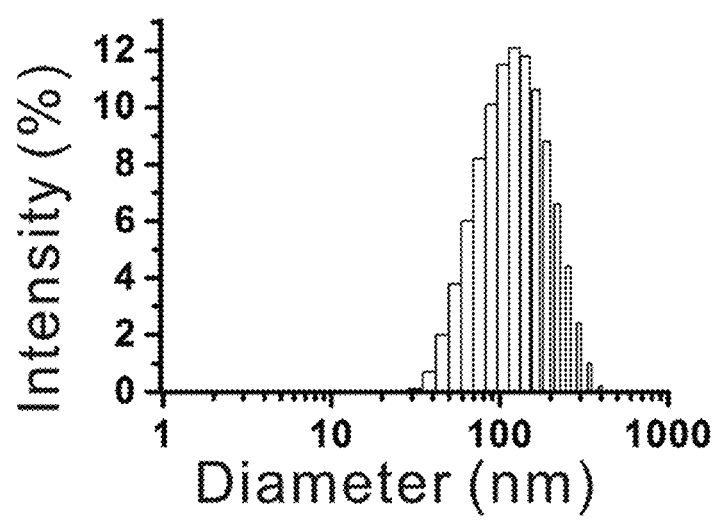
Figure 1G:
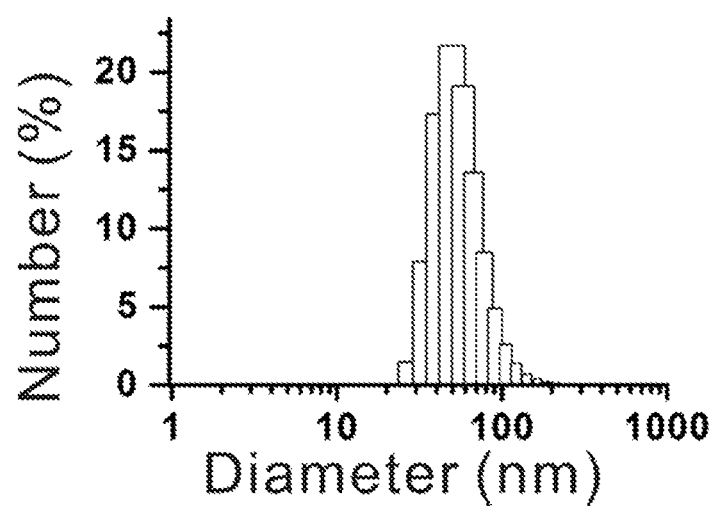

In this example, the morphology of the aggregates was observed by transmission electron microscopy (TEM) (FIG. 1D) and atomic force microscopy (AFM) (FIG. 1E). TEM revealed heterogeneous spherical species with several spheroid-shaped and ring-shaped features, whereas, AFM revealed mostly spheroids but very few ring-shaped structures (FIG. 1E, inset). The particle size distribution was calculated based on TEM images. Majority of the spherical particles measured around 40 to 60 nm in diameter (data not shown). The ring-shaped oligomer examined by AFM was 6 nm in height (data not shown). In addition, dynamic light scattering (DLS) of the oligomer fraction eluted from the SEC also showed a heterogeneous distribution, with the particle size ranging from 40 to 400 nm in diameter (FIG. 1F). The largest population of these particles had a diameter of around 50 to 60 nm (FIG. 1G), which is consistent with the results from the TEM studies. Combining the imaging and size distribution findings, our results showed that full-length TDP-43 formed heterogeneous particles with spherical ultra-structures. The results are consistent with a previous report, suggesting wild type TDP-43 and ALS-linked TDP-43 mutants formed oligomers (Johnson et al., J. Biol. Chem (2009) 284, 20329-20339). In sum, we found that structurally and immunologically, these TDP-43 species closely resembled spherical amyloid oligomers that are widely considered neurotoxic in several neurodegenerative diseases.

Example 3 TDP-43 Oligomers are Conformational and Functional Distinct

Figure 2A:
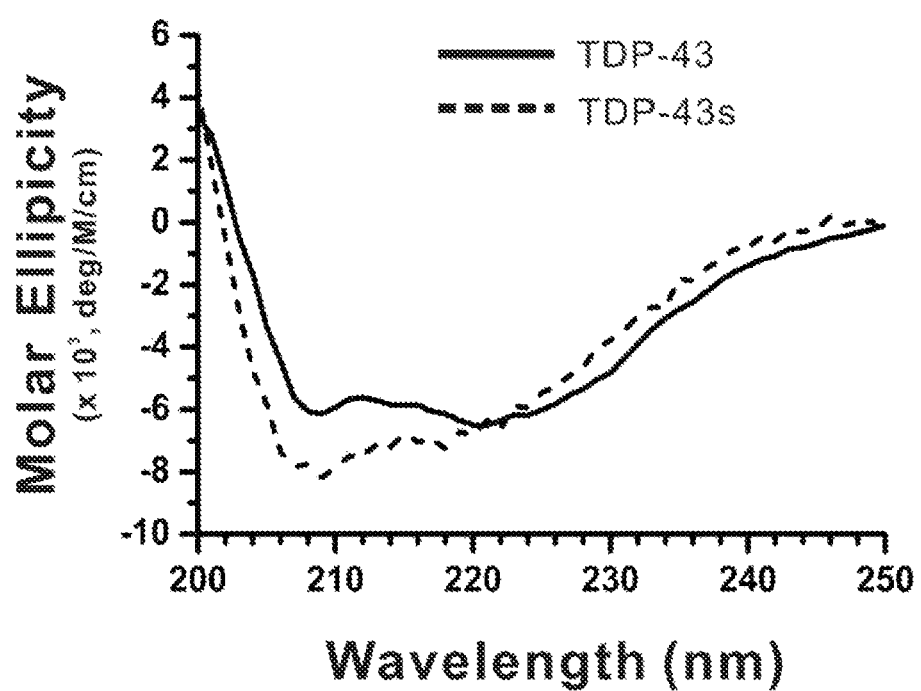
FIGS. 2A-2D depict the conformation, ThT fluorescence, and DNA binding of TDP-43.
Figure 2B:
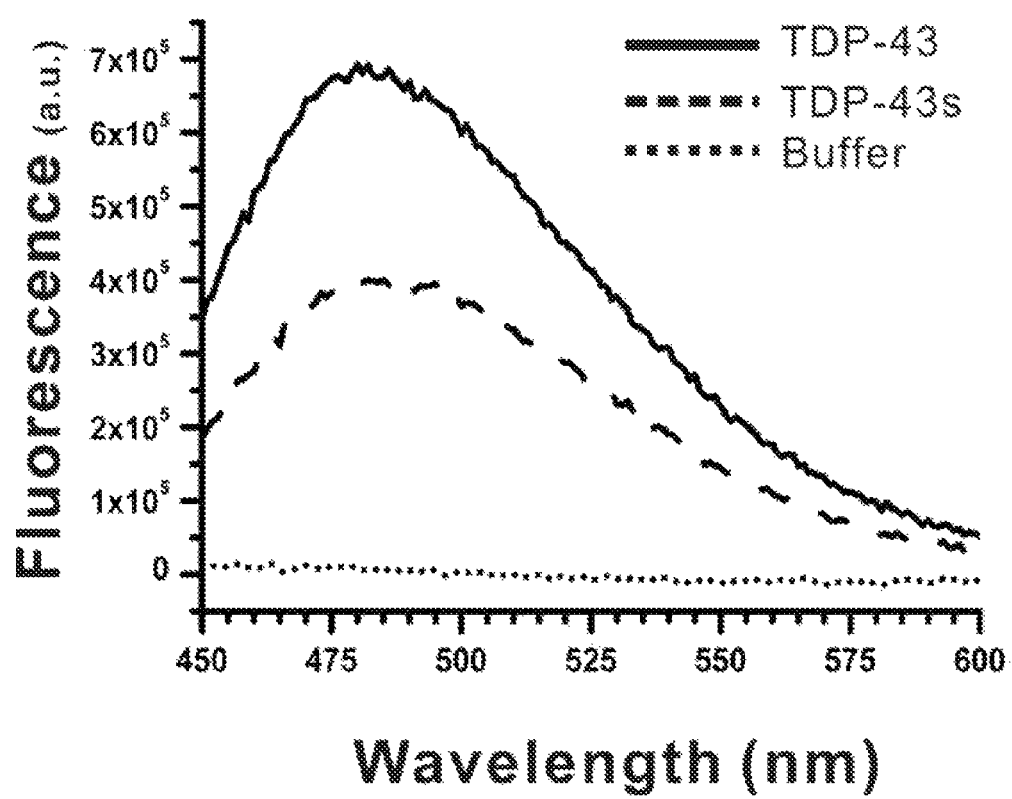

To further examine the TDP-43 oligomers, the secondary structure of TDP-43 oligomers were characterized by far-UV circular dichroism (CD), and results are illustrated in FIG. 2A. Two double minima were respectively observed near 210 and 222 nm, which likely represent α-helical structures. The spectrum differs from that of the short-form mouse TDP-43 (residues 101-265, denoted as TDP-43s in plots), which comprises two RRMs with mostly β-strands in its crystal structure (Kuo et al., Nucleic Acids Res (2009) 37, 1799-1808). The fluorescence spectra resulting from the excitation of the intrinsic aromatic residues showed emission maxima at approximately 340 nm, indicating the tyrosinyl and tryptophanyl residues of TDP-43 were solvent-exposed (data not shown). Furthermore, to detect the exposed hydrophobic protein surfaces, an extrinsic fluorescence dye Bis-ANS that usually probes partially unfolded intermediates upon protein folding was employed, and results are depicted in FIG. 2B. As illustrated in FIG. 2B, the full-length TDP-43 reacted with Bis-ANS to a greater extent than the short-form TDP-43, which further suggest that full-length TDP-43 oligomers possesses different hydrophobic-exposed surface area than the short-form TDP-43.

Figure 2C:
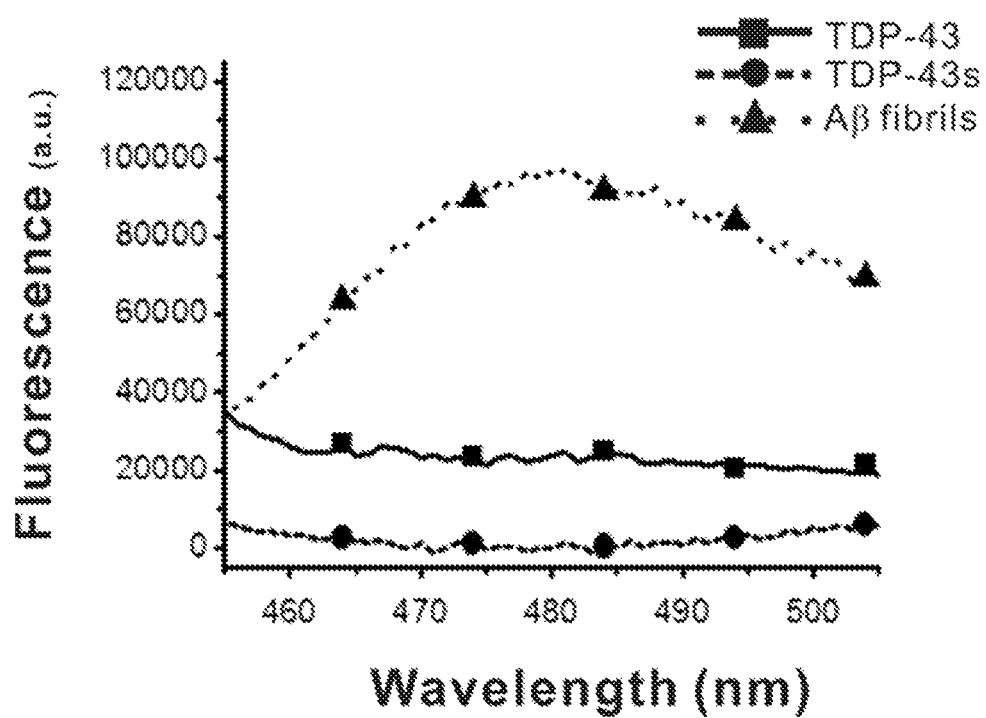

In addition, the classic amyloid dye thioflavin T (ThT) was also used to examine whether full-length TDP-43 binds to ThT, and results are depicted in FIG. 2C. No fluorescence emission peak was found for either full-length or short-form TDP-43 resulting from ThT binding. By contrast, the Aβ fibrils at the same protein concentration, 1 µM, showed strong fluorescence emission (FIG. 2C), which is consistent with the pathological examination result using thioflavin. Similarly, TDP-43 oligomers binding with Congo Red and its immunoreactivity with anti-fibrillar antibody OC all came out negative (data not shown). These results and the CD data suggest that TDP-43 oligomers are unlikely to adopt cross-β sheet structure. However, atomic level structural studies are needed for further characterization.

Figure 2D:
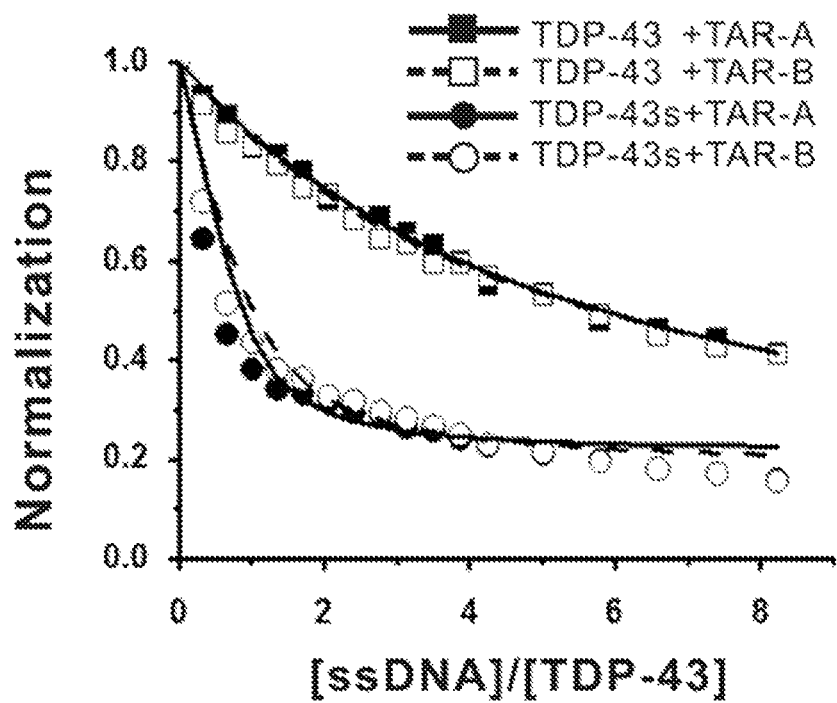

Given that normal, functional TDP-43 binds to a specific nucleic acid sequence, we then investigated whether TDP-43 oligomers would interfere with the DNA binding capability. Fluorescence titration was adopted to monitor protein conformational changes upon DNA binding, and results are illustrated in FIG. 2D. Briefly, TDP-43 oligomers were titrated with single-strand TAR DNA-A or -B sites and compared with the short-form TDP-43 that has been reported to bind these ssDNAs in submicromolar affinity (Kuo et al., Nucleic Acids Res (2009) 37, 1799-1808). As evidenced in FIG. 2D, both TAR DNA-A and -B sites quenched the short-form TDP-43 fluorescence in low ssDNA concentrations, whereas the level of quenching was significantly reduced in full-length TDP-43. The data fitted well with a single protein and ligand binding equation as described in the "Material and Methods" section indicating a 1:1 stoichiometry of TDP-43 and ssDNA. The dissociation constant, Kd, obtained from the fits are 7.05±0.82, 6.27±0.68, 0.20±0.09, and 0.38±0.10 µM for full-length TDP-43 with TAR-A, full-length TDP-43 with TAR-B, short-form TDP-43 with TAR-A, and short-form TDP-43 with TAR-B, respectively. The results indicated that ssDNA binding for the short-form is more than 15 fold stronger than that for the full length TDP-43, in which the TAR-A and -B sites have similar affinities to TDP-43. The finding indicates that RRMs of full-length TDP-43 oligomers either possess abnormal conformations with reduced DNA binding capability or are hindered from DNA binding because of masking of the binding regions. The emission change that remained within the full-length TDP-43 could be attributed to the existence of a small population of TDP-43 monomers in the sample. Taken together, these results demonstrated that TDP-43 oligomers have different biophysical and biochemical properties from those of the short-form TDP-43, indicating their conformations are distinct.

Example 4 TDP-43 Oligomers Convert AO to Amyloid Oligomers

In this example, whether TDP-43 may influence A13 fibrillization pathway was investigated by cross-seeding experiments.

Figure 3A:
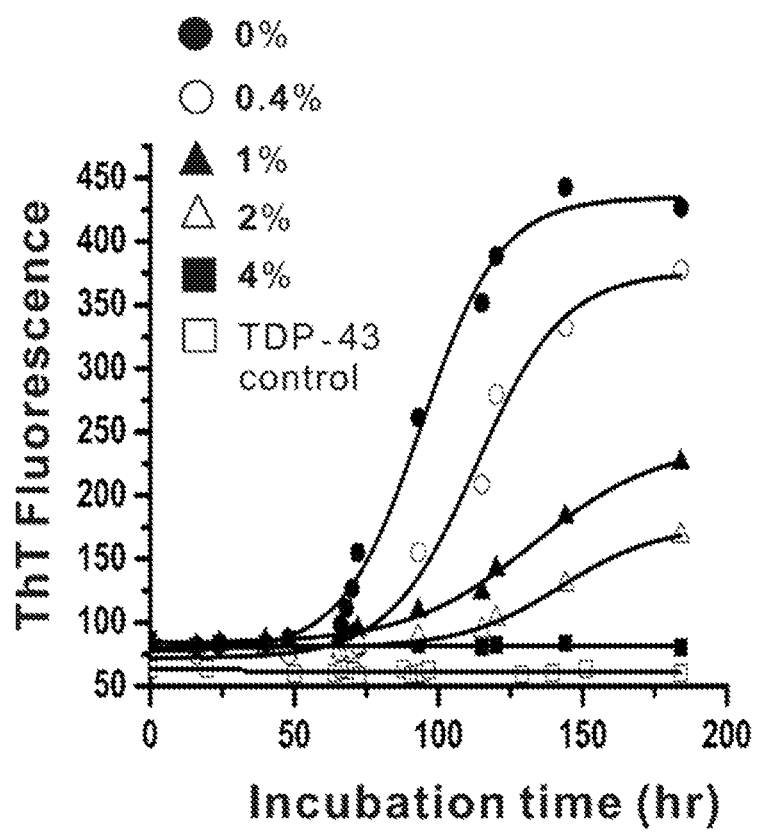
FIGS. 3A-3C depict the cross-seeding of TDP-43 to Aβ.
Figure 3B:
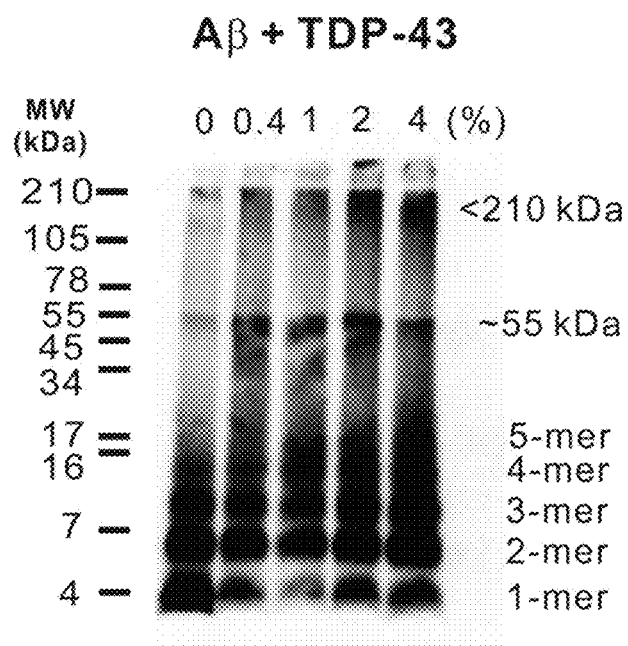
Figure 3C:
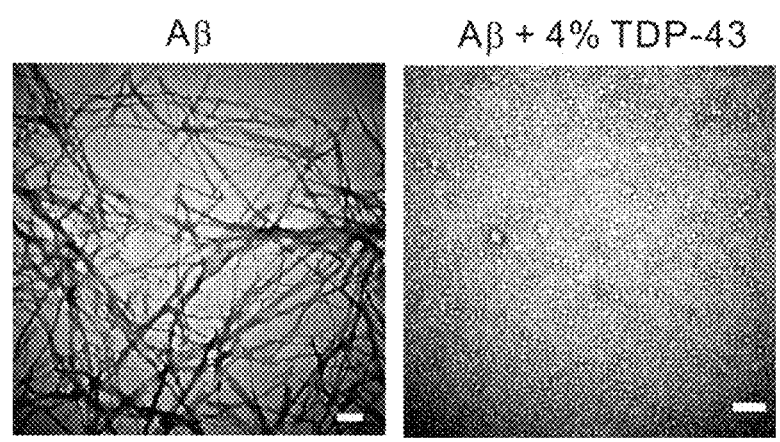

First, Aβ40 fibrillization was examined by ThT assay in the absence and presence of TDP-43 oligomers, ranging from 0.4 to 4%, with results illustrated in FIG. 3A. It was found that TDP-43 potently inhibited Aβ fibrillization in a dose-dependent manner (FIG. 3A). The presence of 4% TDP-43 completely suppressed Aβ fibrillization during the entire experimental time of approximately 180 hr. Photo-induced cross-linking (PICUP) was then performed to examine the transient Aβ species appeared in the starting time point, and results indicated that Aβ alone formed primarily monomers, dimers, trimers, and tetramers after cross-linking, whereas TDP-43 oligomer served to seed more higher-molecular-weight Aβ species (FIG. 3B). Aβ pentamers were observed dose-dependently upon TDP-43 addition. Also, two larger assemblies, migrating at ~55 kDa and smearing from ~105 to >210 kDa, were observed. In addition to the SDS-irresistant TDP-43 monomers, a ~55 kDa species and some species causing a smear from ~80 to >210 kDa were found. Further analysis using TEM imaging showed that Aβ did not undergo fibril formation, but rather was transformed into spherical oligomers with a diameter of <10 nm in the presence of 4% TDP-43 oligomers, whereas Aβ alone still formed mature amyloid fibrils as expected (FIG. 3C). The TDP-43 oligomer seeds retained the diameter of >50 nm which was larger than those of Aβ oligomers (data not shown). These results supported that TDP-43 oligomers can induce the Aβ oligomer formation, indicating again that TDP-43 shares common properties with amyloids.

Example 5 TDP-43 Oligomers Induce Neurite Degeneration and Toxicity

In this example, whether TDP-43 oligomers may cause neurotoxicity and neurite degeneration was investigated.

Figure 4A:
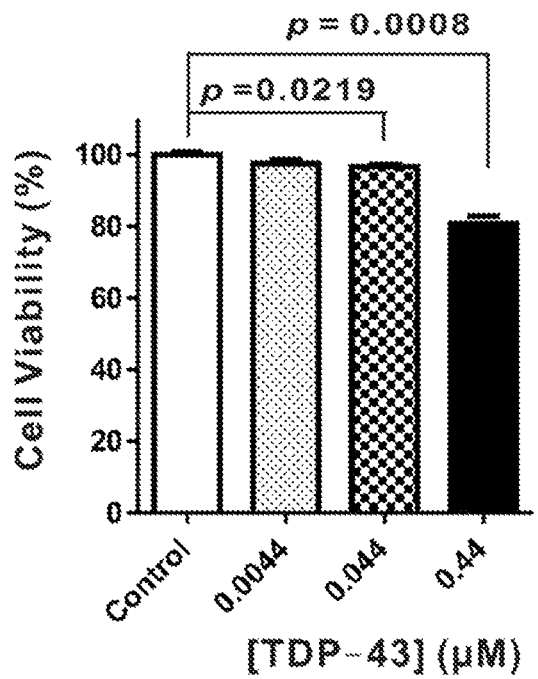
FIGS. 4A-4E depict that TDP-43 oligomers induce neurite degeneration and are neurotoxic in vitro and in vivo. Cytotoxicity of TDP-43 to human BE(2)-C cells performed by MTT (FIG. 4A) and LDH assays (FIG. 4B) (n=3, mean±S.E.M.).
Figure 4B:
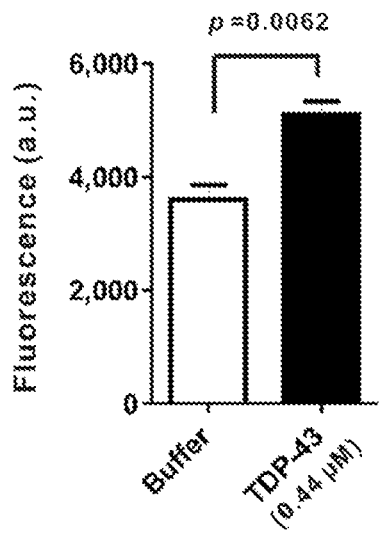
Figure 4C:
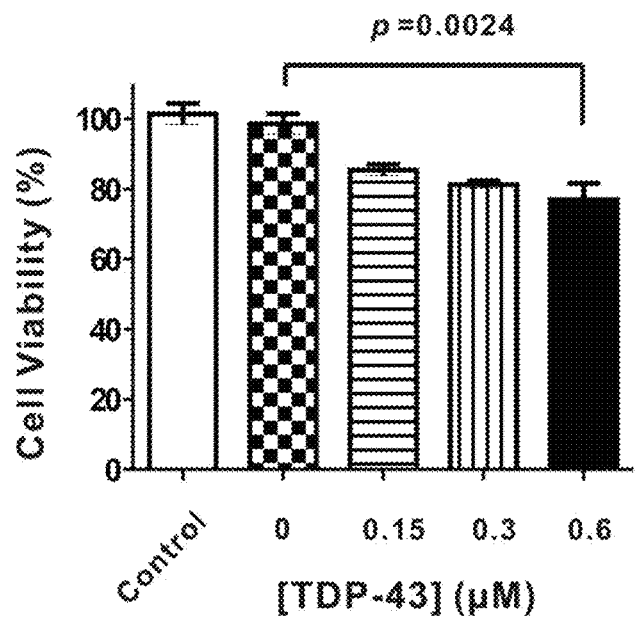

Briefly, human neuroblastoma BE(2)-C cells were treated with serially-diluted TDP-43 sample containing predominantly oligomers, and the cytotoxic effect was examined by MTT and LDH assays, and results are depicted in FIGS. 4A to 4C. MTT assay indicated approximately 20% reduction in cell viability in the presence of 0.44 µM TDP-43, as compared with that of the buffer controls (FIG. 4A). The poor solubility of recombinant TDP-43 made toxicity experiments with higher TDP-43 concentrations impossible. Similar results were found in LDH assay, with 0.44 µM TDP-43 induced a significant level of cell death (FIG. 4B). TDP-43 produced dose-dependent neurotoxicity in the primary cortical neurons of mice, in which 0.6 µM of TDP-43 caused approximately 20% reduction in cell viability (FIG. 4C).

Figure 4D:
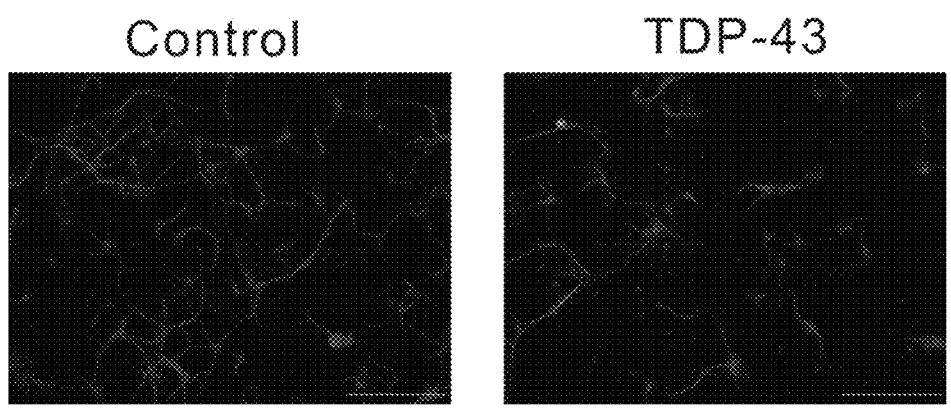
Figure 4E:
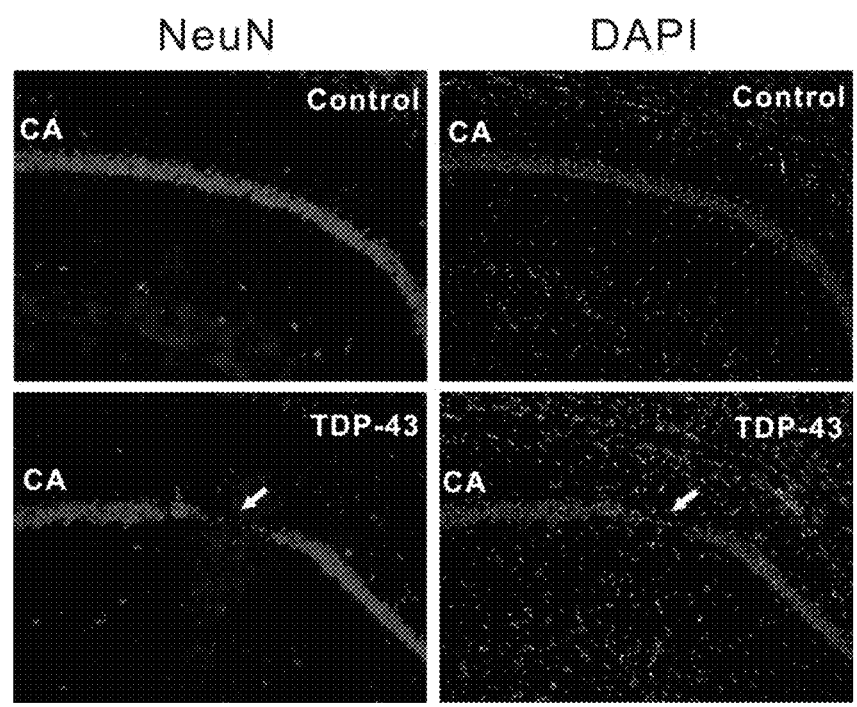

In addition, immunohistochemistry study from the cortical neurons of mice revealed that 0.6 µM TDP-43 induced shrinkage of neurites and reduced neuron density and numbers (FIG. 4D). To further test the neurotoxic effects of TDP-43 oligomers in vivo, 2 µl of 2.2 µM TDP-43 was injected to the hippocampal region of mice and the survival of neuronal cells was examined by immunofluorescence staining. Substantial amount of neuronal cells was found lost in the CA1 layer in TDP-43-injected mice (FIG. 4E), but not in the buffer-injected mice, as determined by the neuronal marker NeuN immunoreactivity and DAPI staining. The result indicated that injection of recombinant full-length TDP-43 oligomers in the hippocampus does induce toxicity.

Example 6 Production and Characterization of TDP-43 Oligomer-Specific Polyclonal Antibody Since the anti-amyloid oligomer antibody (i.e., A11) cross-reacted with different amyloids, to validate whether the TDP-43 oligomers are present in the disease, a polyclonal antibody were generated using the recombinant TDP-43 oligomers as immunogen in rabbit in accordance with procedures described in "Materials and Methods" section, and the thus obtained polyclonal antibody is named TDP-O.

Figure 5A:
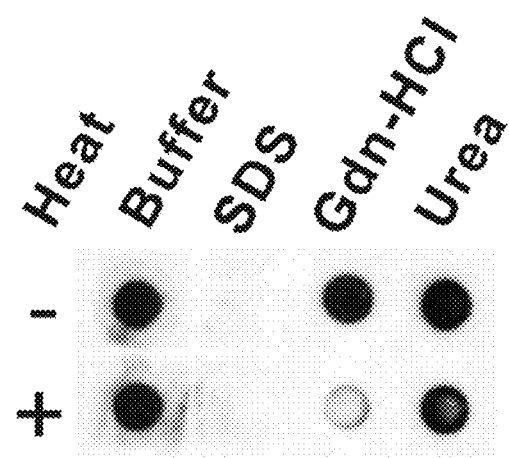
FIGS. 5A-5E depict that TDP-O antibody recognizes TDP-43 oligomers specifically.

The specificity of TDP-O antibody against the full-length TDP-43 oligomeric conformation was examined by dot blotting under various denaturing conditions as described in "Materials and Methods" section, and results are illustrated in FIG. 5A. TDP-O with 1:125,000 dilution was capable of reacting with full-length TDP-43 in the native buffer regardless of heating (90° C., 1 h); however, the reactivity between the antibody and the TDP-43 oligomer disappeared when 2% SDS was present, with or without heating. Further, the reactivity did not diminish when the full-length TDP-43 was treated with either 7.2 M GdnHCl or 9 M urea at room temperature for more than one hr, which indicated that the protein was stable under high concentration of chemical denaturants; however, the reactivity signal started to decrease when additional heating was employed, indicating that TDP-O is a conformational dependent antibody. In sum, the dot blotting result from TDP-O was qualitatively identical to that of A11 (FIG. 5A vs FIG. 1C).

Figure 5B:
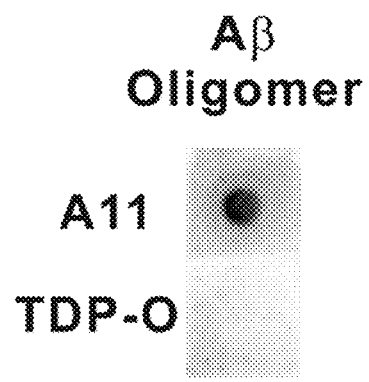
Figure 5C:
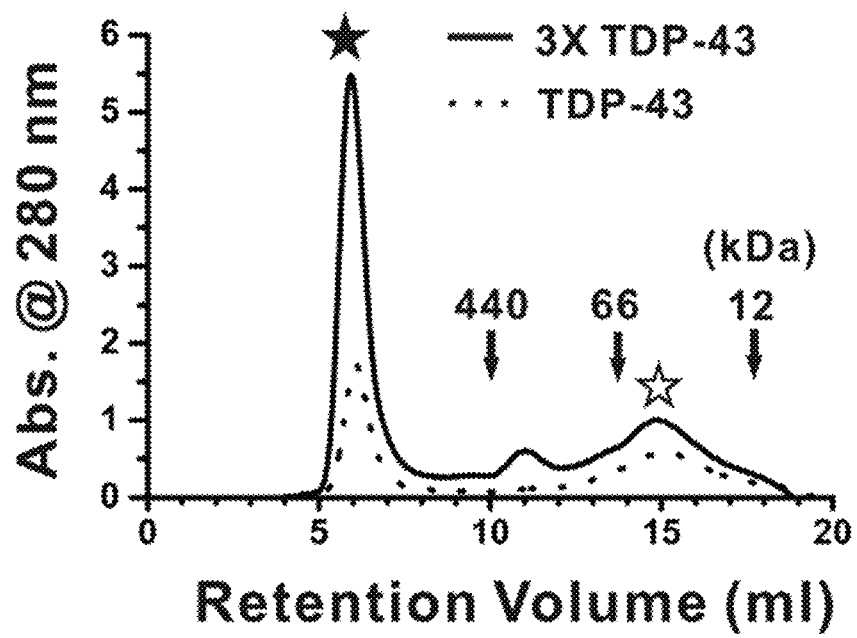
Figure 5D:
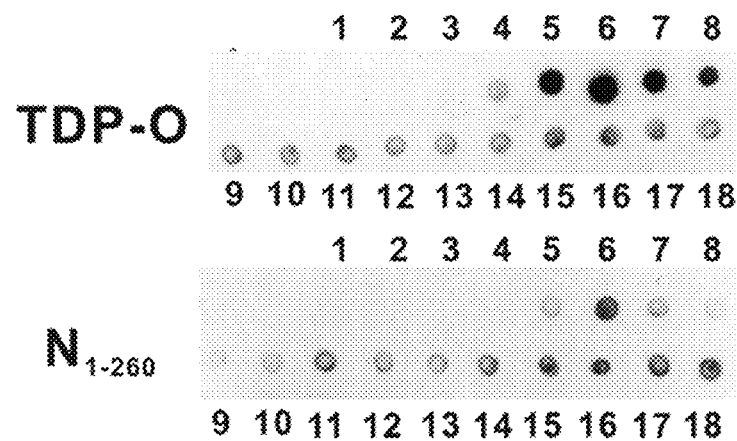

To test whether TDP-O is TDP-43 specific rather than a common amyloid oligomer antibody like A11, the antibody specificity against Aβ oligomers was examined using A11 and/or TDP-O. As depicted in FIG. 5B, TDP-O failed to recognize Aβ oligomers, which demonstrates that it is specific toward TDP-43 oligomers. ELISA was also performed to quantitatively characterize the reactivity between TDP-O and TDP-43 oligomers and monomers; while the TDP-43 antibody recognizing N-terminal residues 1-260 ($N_{1-260}$) was employed for comparison purpose. To prepare the oligomer and monomer fractions of the full-length TDP-43, the full-length TDP-43 at approximately 1 μM or three times more concentrated TDP-43 samples was loaded into SEC, and 1 ml eluted fractions were collected (FIG. 5C). The SEC fractions of the concentrated TDP-43 from fractions 1 to 18 were then subjected to dot blotting with TDP-O or $N_{1-260}$ antibodies, and results are illustrated in FIG. 5D. It was found that TDP-O reacted strongly with fraction numbers 5 to 7, which corresponded to the TDP-43 oligomers eluted in the void volume. By contrast, $N_{1-260}$ exhibited strong reactivity with fraction 6, and fractions 15 to 18; which indicates that this antibody may recognize both oligomeric and monomeric form of TDP-43.

Figure 5E:
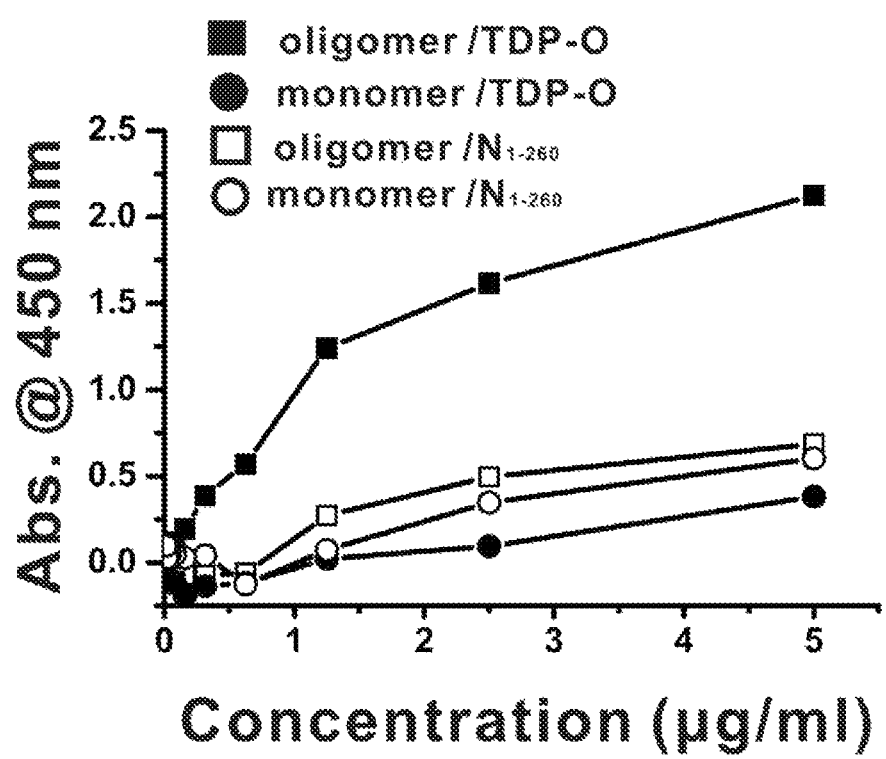

Further, the TDP-43 oligomer specificity with TDP-O was quantified by ELISA, where the $N_{1-260}$ antibody was used as control. After protein quantification by micro-BCA assay, the TDP-43 oligomer and monomer fractions were respectively coated onto ELISA plate with serial dilutions. TDP-O and $N_{1-260}$ were applied and developed following standard ELISA protocol. Results depicted in FIG. 5E indicated that TDP-O antibody exhibited strong reactivity towards TDP-43 oligomers (EC50<0.5 μg/ml) than to TDP-43 monomer, whereas $N_{1-260}$ antibody exhibited similar reactivity toward ether TDP-43 oligomer or monomer (FIG. 5E). Further, to insure TDP-O recognizes the oligomeric rather than fibrillar form of TDP-43 as previously reported (Wang et al., J Biol Chem (2013) 288, 9049-9057), the β5 fibrils generated from the $5^{th}$ β-strand within RRM2 domain of TDP-43 were dotted (data not shown), and result clearly showed that TDP-O recognizes only TDP-43 oligomers but not the β5 fibrils. Taken together, the polyclonal TDP-O antibody of this application may specifically recognize TDP-43 oligomeric conformation without cross-reacting with Aβ species.

Example 7 TDP-43 Oligomers Exist in Transgenic Mice Brain

Figure 6A:
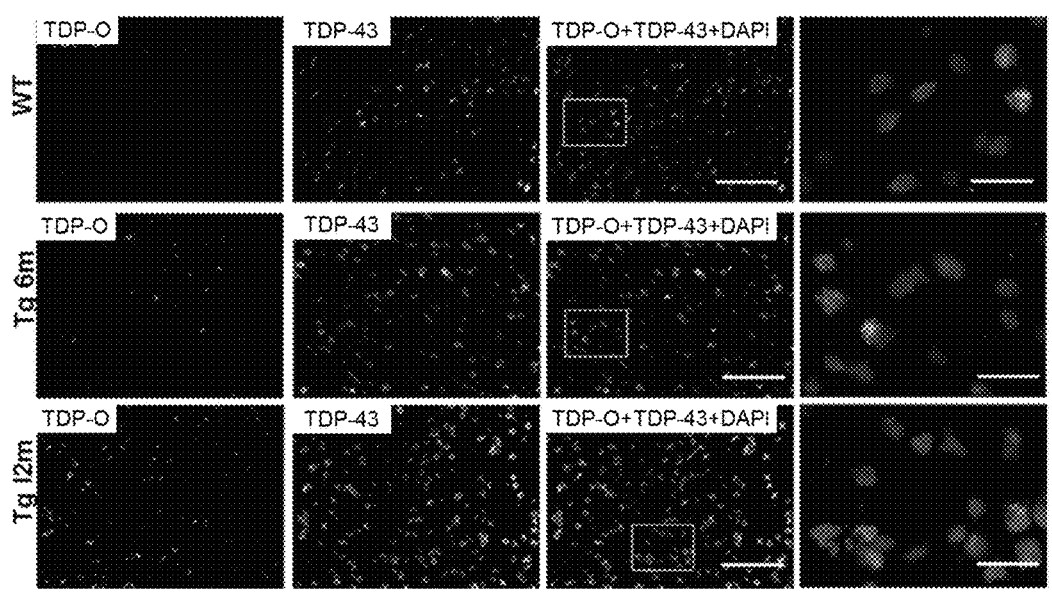
FIGS. 6A-6B depict that TDP-43 oligomers are present and increase with age in transgenic mouse model of FTLD-TDP.
Figure 6B:
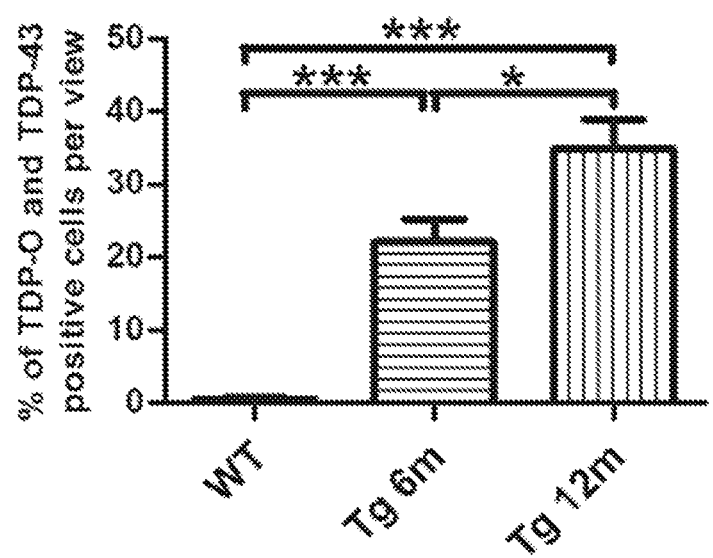

To examine the presence of TDP-43 oligomers in vivo, immunohistochemical staining on the brain sections of wild type mice and FTLD-TDP-43 transgenic mice at 6 and 12 month of age was performed, and results are illustrated in FIGS. 6A and 6B. FTLD-TDP-43 transgenic mice expressing full-length TDP-43 in the forebrain has been reported to recapitulate FTLD-TDP-like pathology (Tsai et al., J Exp Med (2010) 207, 1661-1673), for their deficiency in the learning/memory capabilities and motor functions as they age. In this example, the brain sections of FTLD-TDP-43 transgenic mice were immunofluorescently stained with anti-TDP-43 and TDP-O and counterstained with DAPI. As expected, in the wild type mice, TDP-43 was found predominantly in the nucleus. By contrast, TDP-43 was mainly found in the cytosol in the FTLD-TDP transgenic mice, while TDP-O signals were also detected. Significant amount of TDP-43 and TDP-O signals were found to colocalize in the cells, and number of cells with double positive signals increased with age. The appearance and colocalization of the signals suggested that amyloid-like TDP-43 oligomers do exist in the FTLD-TDP transgenic mice brain and the amount increases with age.

Example 8 TDP-43 Oligomers are Present in Brains of FTLD-TDP Patients

Figure 7:
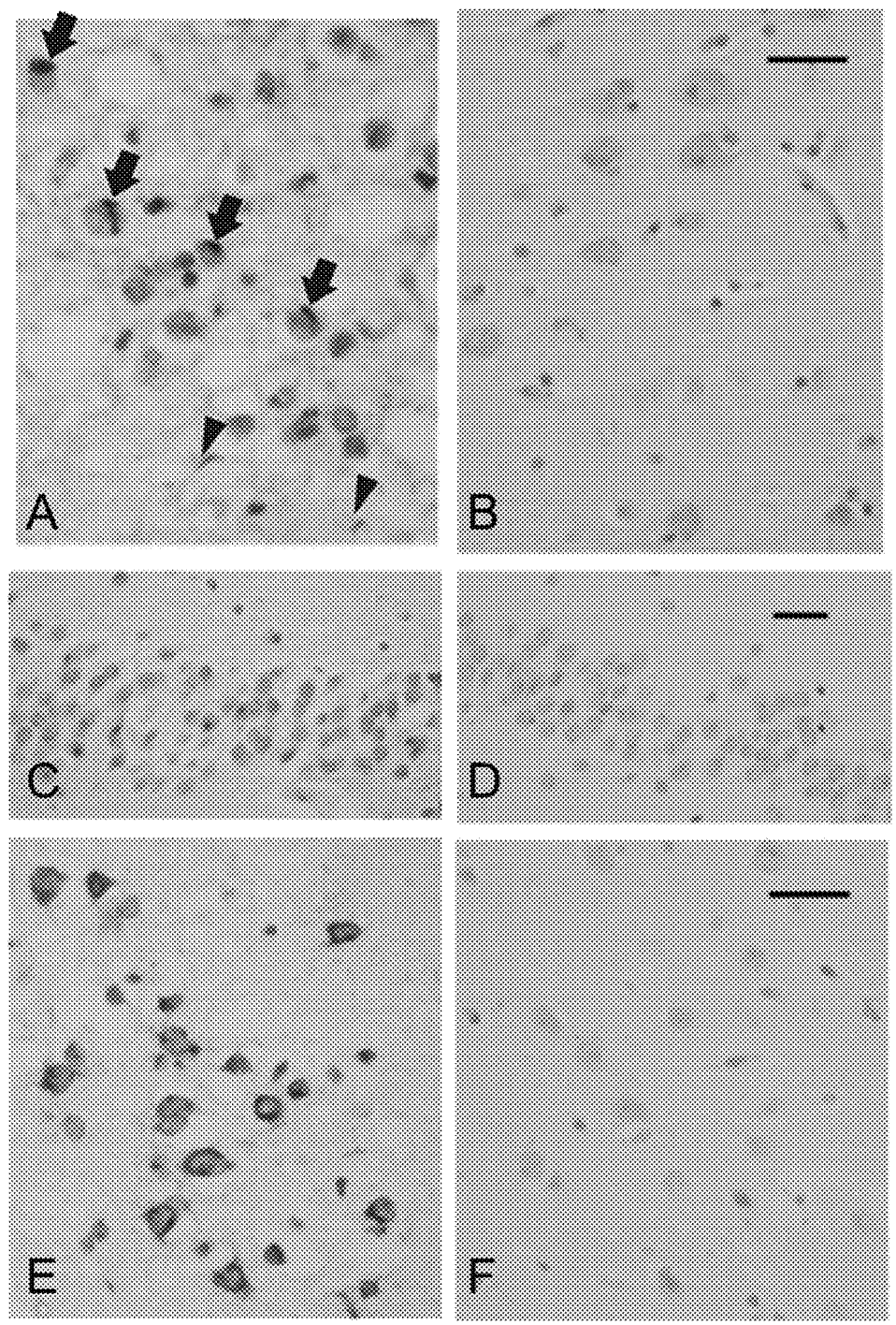
FIG. 7 depicts that TDP-43 oligomers are present in FTLD-TDP patients. A total of three FTLD-TDP cases, three neurologically and pathologically normal age-matched controls, and three Alzheimer's disease cases without TDP-43 inclusions (as "neurodegenerative disease controls") were examined. Representative images are shown. (A), (C), and (E) Immunohistochemical staining of TDP-43 in the hippocampal (C) and frontal cortical sections (A, E) of FTLD-TDP patients by the TDP-O antibody. TDP-O identified densely stained, ovoid or irregularly shaped but discreet cytoplasmic inclusions (arrow) as well as comma-shaped profiles in the neuropil representing dystrophic neurites (arrowhead). In some cortical areas such as shown in (E), neuronal cytoplasm showed coarse granular immunoreactivities. (B), (D), and (F) TDP-O did not stain the brains of control subjects. TDP-O antibody, in contrast to antibodies for monomeric TDP-43, did not stain nuclei demonstrating specificity toward misfolded TDP-43. Scale bars in all panels are 20 µm.
Figure 8A:
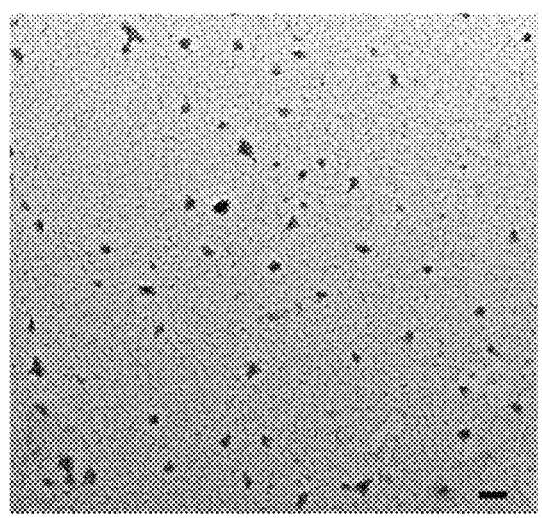
FIGS. 8A-8B depict the immunogold labeling of TDP-43 oligomers immunoprecipitated from the diseased hippocampus. The hippocampus of a FTLD-TDP patient was extracted and immunoprecipitated by TDP-O antibody. The eluent was subjected to EM with immunogold labeling with the N-term TDP-43 antibody (scale bar, 50 nm).
Figure 8B:
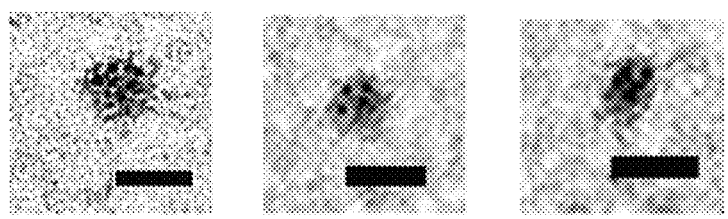
Figure 8B:
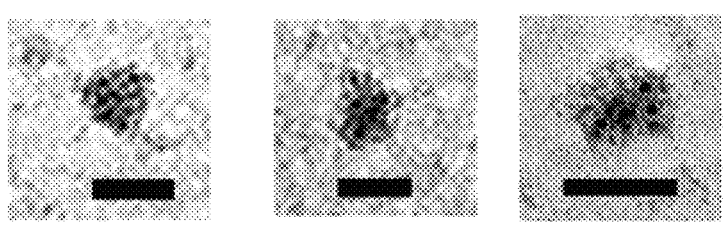

To evaluate the relevance of TDP-43 oligomers in human diseases, the presence of TDP-43 oligomers in FTLD-TDP patients was investigated using the subgroup of FTLD patients with TDP-43 immunoreactive inclusions. The TDP-O polyclonal antibodies were used to immunostain hippocampal and frontal cortical sections of three cases of pathologically confirmed FTLD-TDP, three cases of age-matched non-dementic controls, and three cases of pathologically confirmed AD without TDP-43 pathology as the "disease controls". The TDP-O antibody identified various neuronal cytoplasmic inclusions (FIG. 7, panels A and C) and dystrophic neurites (FIG. 7, panel A) that appeared to be similar to the TDP-43 inclusions in FTLD-TDP patients. In some areas, neuronal cytoplasm was intensively stained in a granular pattern (FIG. 7, panel E). By contrast, except the non-specific reactivities from neuronal lipofuscin, TDP-O did not exhibit significant immune-reactivity towards the control brains (FIG. 7, panels B, D, and F), nor to AD brains lacking TDP-43 pathology (data not shown). TDP-O polyclonal antibody failed to stain the nuclei in normal tissue, which is consistent with our biochemical observation that it does not react with TDP-43 monomer normally present in the nuclei. In addition, to validate the morphology of TDP-43 recognized by TDP-O polyclonal antibody, we performed immunoprecipitation (IP) by TDP-O with the control and diseased human hippocampus. The Triton soluble fractions of hippocampus were prepared and subjected to IP with cross-linked TDP-O polyclonal antibody. The eluent was subjected to EM immunolabeled with N-terminal TDP-43 antibody ($N_{1-260}$) (FIGS. 8A and 8B). We successfully observed rounded, spherical TDP-43 aggregates with a diameter of approximately 50 nm in the diseased sample but not in the control sample, and the species were recognized by $N_{1-260}$ antibody indicating that they are not N-terminal truncated. Overall, by using our TDP-O polyclonal antibody, we demonstrated that TDP-43 oligomers exist in the brains of FTLD-TDP patients.

Example 9 Production and Characterization of TDP-43 Oligomer-Specific Monoclonal Antibody (mAb)

Figure 9:
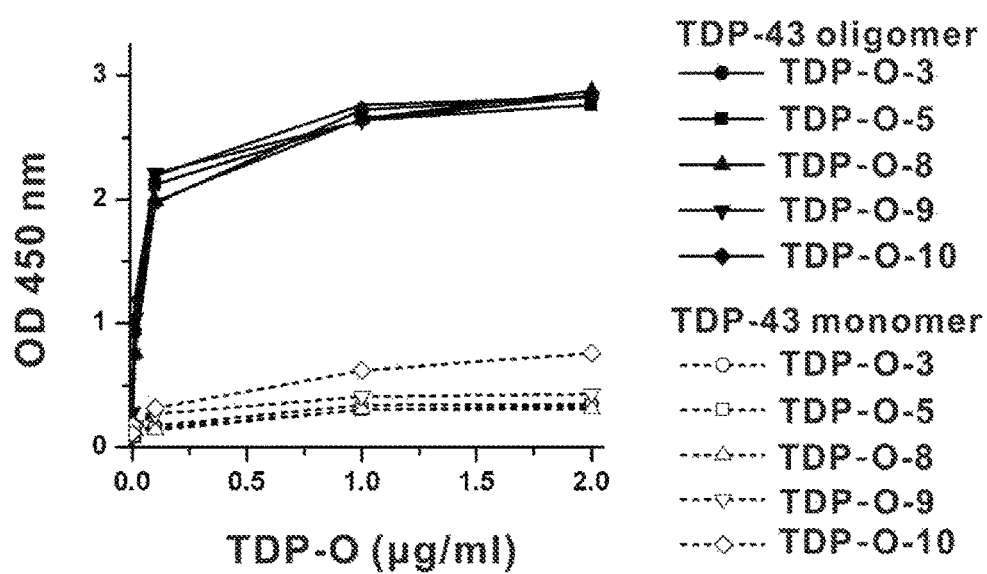
FIG. 9 depicts that TDP-O mAbs exhibit higher specificities toward TDP-43 oligomer. Various concentrations of TDP-O mAbs ($1-2 \times 10^{-5}$ µg/mL) respectively produced by TDP-O-3, -5, -8, -9, and -10 hybridoma cells were used in ELISA assay to detect the SDS denatured or non-denatured TDP-43.

In this example, ELISA assay was performed to examine the specificity of each mAbs produced from TDP-O-3, -5, -8, -9, and -10 hybridoma cells on TDP-43 oligomers with or without SDS denaturation. Results are depicted in FIG. 9. Monoclonal antibodies produced from any of the five hybridoma cell lines exhibited higher binding activities toward non-denatured TDP-43 oligomers than the denatured TDP-43 protein. The results indicated that these mAbs have specificity toward TDP-43 oligomers and they are conformational-dependent antibodies.

Figure 10A:
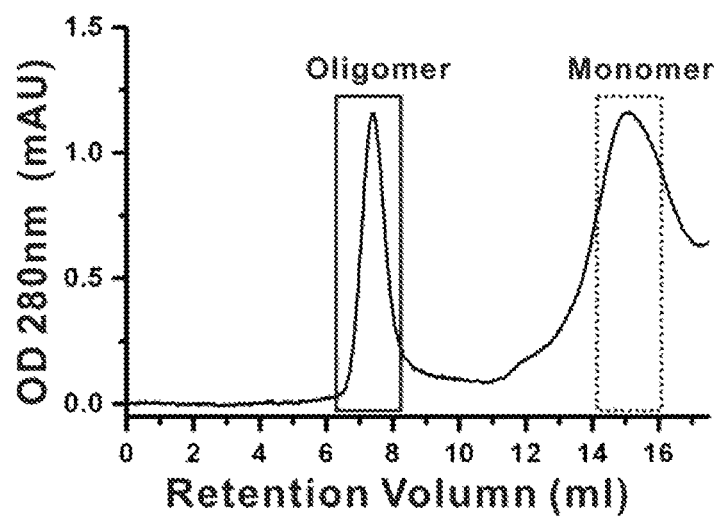
FIGS. 10A-10B depict that TDP-O mAbs exhibit higher specificities toward purified TDP-43 oligomer. The conditional medium of TDP-O hybridoma cells were used to detect purified TDP-43 oligomers and monomers from size-exclusion chromatography by ELISA assay.
Figure 10B:
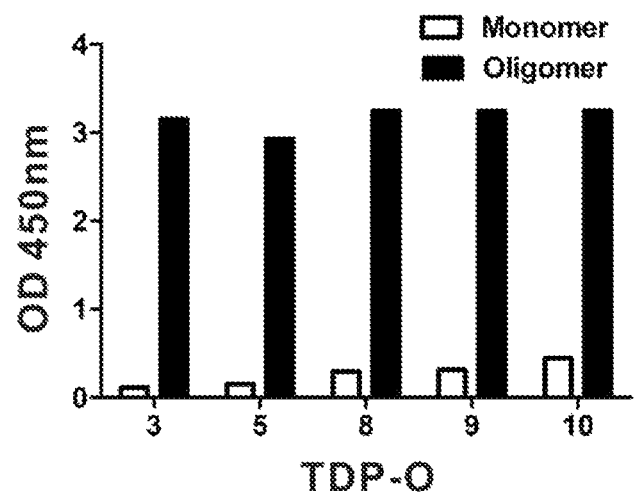

To confirm the binding specificity of the isolated mAbs, TDP-43 oligomers and monomers were purified by gel filtration (FIG. 10A), and then respectively coated on plates for ELISA to confirm the specificity of each mAbs. Results as depicted in FIG. 10B confirmed that each of the mAbs produced from TDP-O-3, -5, -8, -9, and -10 hybridoma cell lines may specifically recognize TDP-43 oligomers.

ELISA mouse mAb isotyping Kit (Thermo) was also used to determine the isotypes of the TDP-O mAbs. Results are summarized in Table 1.

TABLE 1

Isotypes of TDP-O mAbs

| OD 450 nm | TDP-O-3 | TDP-O-5 | TDP-O-8 | TDP-O-9 | TDP-O-10 |
|---|---|---|---|---|---|
| $IgG_1$ | 0.2101 | 0.2261 | 0.1271 | 0.1717 | 0.2299 |
| $IgG_{2a}$ | 1.0523 | 1.2430 | 0.9270 | 1.0333 | 1.1781 |
| $IgG_{2b}$ | 0.0565 | 0.0520 | 0.0509 | 0.0564 | 0.0755 |
| $IgG_3$ | 0.0581 | 0.0539 | 0.0509 | 0.0556 | 0.0757 |
| IgA | 0.0563 | 0.0498 | 0.0533 | 0.0533 | 0.0680 |
| IgM | 0.0565 | 0.0502 | 0.0490 | 0.0519 | 0.0710 |
| Kappa | 2.1870 | 2.6605 | 2.2863 | 1.9313 | 2.3966 |
| Lamda | 0.0574 | 0.0603 | 0.0513 | 0.0572 | 0.0801 |

According to results presented in Table 1, the mAbs produced by TDP-O-3, -5, -8, -9, and -10 hybridoma cell lines are more reactive toward $IgG_{2a}$ and kappa light chain. Therefore, these mAbs belongs to $IgG_{2a}$ and kappa light chain subclasses.

The 5 mAbs thus isolated were subjected to sequence analysis, and consensus sequence were determined and depicted in FIG. 11.

Figure 12:
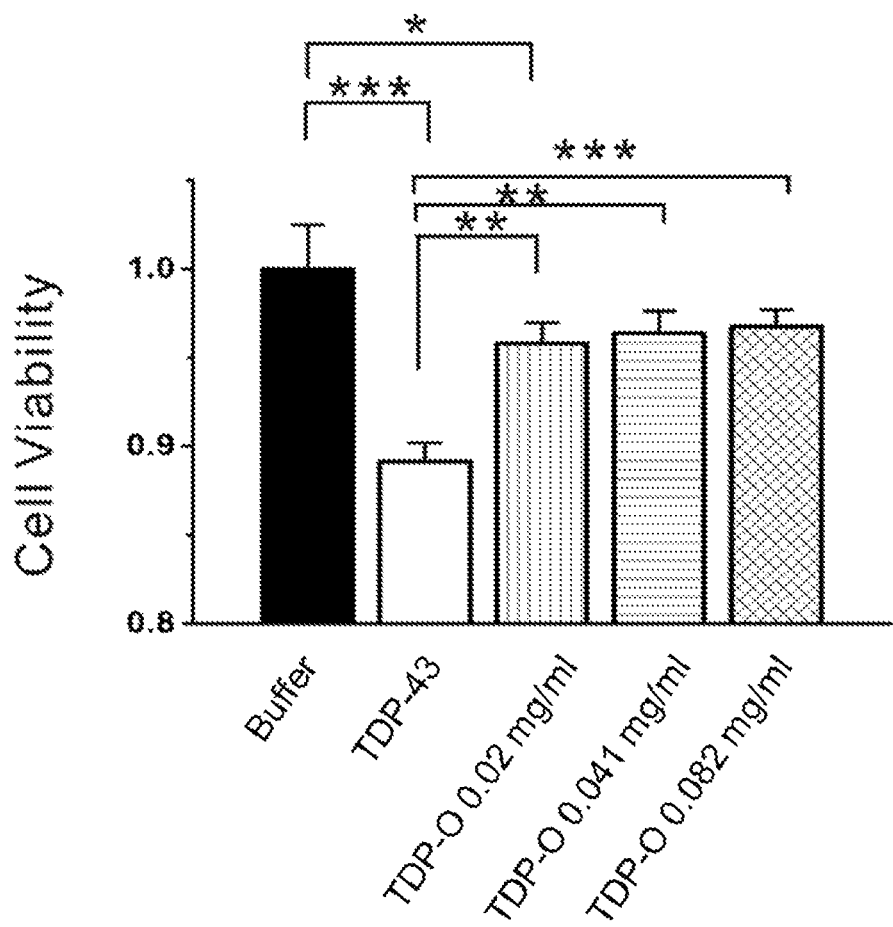
FIG. 12 depicts that TDP-O monoclonal antibody rescues TDP-43 oligomers-induced cytotoxicity. MTT assay was performed to examine cell viability of BE(2)-C cells. Data are presented as mean±standard deviation. Statistical analysis was performed by one-way ANOVAs, $*p<0.05$, $p<0.01$, $*p<0.001$. The result showed the toxicity induced by TDP-43 oligomers was significantly rescued by the treatment of TDP-O antibody.

Example 10 TDP-43 Oligomer-Specific mAb Inhibits TDP-43 Oligomers-Induced Cytotoxicity To examine whether TDP-O antibody can inhibit the cell cytotoxicity induced by TDP-43 oligomers, human neuroblastoma BE(2)-C cells were respectively treated by TDP-43 oligomers with or without monoclonal TDP-O antibody (i.e., TDP-O-3) at the indicated dosages as described in "Materials and Methods". The cell viability was then measured by MTT assay. The result indicated that TDP-43 oligomers induced significant toxicity towards BE(2)-C cells, and such cytotoxic phenomenon was successfully reversed by the administration of TDP-O antibody (FIG. 12).

In conclusion, the present disclosure unexpectedly discovers a pathological form of TDP-43, which cross-seeds Aβ to form amyloid oligomers and is associated with neurodegenerative diseases. Accordingly, the present disclosure aims at providing an antibody useful in suppressing the TDP-43 proteinopathy. Results from the foregoing working examples confirm and support that the present anti-TDP-43 antibodies specifically bind to the pathological form of TDP-43 and suppress the TDP-43-induced cytotoxicity; thus, they may act as a potential means to prevent and/or treat the TDP-43-associated neurodegenerative diseases.

It will be understood that the above description of embodiments is given by way of example only and that various modifications may be made by those with ordinary skill in the art. The above specification, examples and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of this invention.

---

What is claimed is:

1. An antibody or a fragment thereof that specifically binds to a transactivation responsive (TAR)-DNA-binding protein 43 kDa (TDP-43) oligomer comprising,
   a heavy chain variable region comprising the amino acid sequences of SEQ ID NO: 1, SEQ ID NO: 2 and SEQ ID NO: 3; and
   a light chain variable region comprising the amino acid sequences of SEQ ID NO: 5, SEQ ID NO: 6 and SEQ ID NO: 7.

2. The antibody of claim 1, wherein the heavy chain variable region has the amino acid sequence of SEQ ID NO: 4, and the light chain variable region has the amino acid sequence of SEQ ID NO: 8.

3. The antibody of claim 1, wherein the TDP-43 oligomer has a spherical particle size of about 2 to 400 nm in diameter.

4. The antibody of claim 3, wherein the TDP-43 oligomer has a particle size that is about 40 to 60 nm in diameter.

5. A pharmaceutical composition for the prophylaxis or treatment of a TDP-43 oligomer associated disease comprising the antibody of claim 1; and a pharmaceutically acceptable carrier.

6. The pharmaceutical composition of claim 5, wherein the TDP-43 oligomer associated disease is Alzheimer's disease, argyrophilic grain disease, amyotrophic lateral sclerosis (ALS), ALS-parkinsonism dementia complex of Guam, vascular dementia, frontotemporal dementia, semantic dementia, dementia with Lewy bodies, Huntington's disease, Spinocerebellar ataxia, inclusion body myopathy, inclusion body myositis, hippocampal sclerosis, or Parkinson's disease.

7. The pharmaceutical composition of claim 5, wherein the heavy chain variable region has the amino acid sequence of SEQ ID NO: 4, and the light chain variable region has the amino acid sequence of SEQ ID NO: 8.

8. A method of diagnosing a TDP-43 oligomer associated disease from a biological sample of a subject, comprising:
   determining the amount of the TDP-43 oligomer in the biological sample by contacting the biological sample with an effective amount of the antibody of claim 1; and
   comparing the detected amount of the TDP-43 oligomer in the biological sample with that of a control sample obtained from a healthy subject;
   wherein a significantly higher amount of the detected TDP-43 oligomer in the biological sample than that of the control sample indicates that the subject suffers from the TDP-43 oligomer associated disease.

9. The method of claim 8, wherein the TDP-43 oligomer associated disease is Alzheimer's disease, argyrophilic grain disease, amyotrophic lateral sclerosis (ALS), ALS-parkinsonism dementia complex of Guam, vascular dementia, frontotemporal dementia, semantic dementia, dementia with Lewy bodies, Huntington's disease, Spinocerebellar ataxia, inclusion body myopathy, inclusion body myositis, hippocampal sclerosis, or Parkinson's disease.

10. The method of claim 8, wherein the biological sample is a brain biopsy sample, a cerebrospinal fluid sample, a whole blood sample, a serum sample, or a plasma sample.

11. The method of claim 8, wherein the heavy chain variable region has the amino acid sequence of SEQ ID NO: 4, and the light chain variable region has the amino acid sequence of SEQ ID NO: 8.

* * * * *

SEQUENCE LISTING

```
<160> NUMBER OF SEQ ID NOS: 10

<210> SEQ ID NO 1
<211> LENGTH: 8
<212> TYPE: PRT
<213> ORGANISM: Artificial Sequence
<220> FEATURE:
<223> OTHER INFORMATION: VH region-CDR1
<220> FEATURE:
<221> NAME/KEY: VARIANT
<222> LOCATION: 3,5,6
<223> OTHER INFORMATION: Xaa is any of amino acid

<400> SEQUENCE: 1

Gly Tyr Xaa Phe Xaa Xaa Tyr Trp
1               5

<210> SEQ ID NO 2
<211> LENGTH: 8
<212> TYPE: PRT
```

```
<213> ORGANISM: Artificial Sequence
<220> FEATURE:
<223> OTHER INFORMATION: VH region-CDR2
<220> FEATURE:
<221> NAME/KEY: VARIANT
<222> LOCATION: 4,6,7,8
<223> OTHER INFORMATION: Xaa is any of amino acid

<400> SEQUENCE: 2

Ile Asn Pro Xaa Thr Xaa Xaa Xaa
1               5

<210> SEQ ID NO 3
<211> LENGTH: 13
<212> TYPE: PRT
<213> ORGANISM: Artificial Sequence
<220> FEATURE:
<223> OTHER INFORMATION: VH region-CDR3
<220> FEATURE:
<221> NAME/KEY: VARIANT
<222> LOCATION: 1,7
<223> OTHER INFORMATION: Xaa is any of amino acid

<400> SEQUENCE: 3

Xaa Arg Gly Gly Lys Tyr Xaa Gly Gly Ala Met Asp Tyr
1               5                   10

<210> SEQ ID NO 4
<211> LENGTH: 109
<212> TYPE: PRT
<213> ORGANISM: Artificial Sequence
<220> FEATURE:
<223> OTHER INFORMATION: VH region
<220> FEATURE:
<221> NAME/KEY: VARIANT
<222> LOCATION: 18,23,24,25,28,30,31,37,54,56,57,58,60,63,67,69,74,77,
      81,84,95,97,103
<223> OTHER INFORMATION: Xaa is any of amino acid

<400> SEQUENCE: 4

Gln Val Gln Leu Gln Gln Ser Gly Ala Glu Leu Ala Lys Pro Gly Ala
1               5                   10                  15

Ser Xaa Lys Met Ser Cys Xaa Xaa Xaa Gly Tyr Xaa Phe Xaa Xaa Tyr
            20                  25                  30

Trp Met His Trp Xaa Lys Gln Arg Pro Gly Gln Gly Leu Glu Trp Ile
        35                  40                  45

Gly Tyr Ile Asn Pro Xaa Thr Xaa Xaa Xaa Glu Xaa Asn Gln Xaa Phe
    50                  55                  60

Lys Asp Xaa Ala Xaa Leu Thr Ala Asp Xaa Ser Ser Xaa Thr Ala Tyr
65                  70                  75                  80

Xaa Gln Leu Xaa Ser Leu Thr Ser Glu Asp Ser Ala Val Tyr Xaa Cys
                85                  90                  95

Xaa Arg Gly Gly Lys Tyr Xaa Gly Gly Ala Met Asp Tyr
                100                 105

<210> SEQ ID NO 5
<211> LENGTH: 5
<212> TYPE: PRT
<213> ORGANISM: Artificial Sequence
<220> FEATURE:
<223> OTHER INFORMATION: VL region-CDR1
<220> FEATURE:
<221> NAME/KEY: VARIANT
<222> LOCATION: 4
<223> OTHER INFORMATION: Xaa is any of amino acid

<400> SEQUENCE: 5
```

```
Ser Ser Val Xaa Tyr
1               5

<210> SEQ ID NO 6
<211> LENGTH: 3
<212> TYPE: PRT
<213> ORGANISM: Artificial Sequence
<220> FEATURE:
<223> OTHER INFORMATION: VL region-CDR-2
<220> FEATURE:
<221> NAME/KEY: VARIANT
<222> LOCATION: 1
<223> OTHER INFORMATION: Xaa is any of amino acid

<400> SEQUENCE: 6

Xaa Thr Ser
1

<210> SEQ ID NO 7
<211> LENGTH: 9
<212> TYPE: PRT
<213> ORGANISM: Artificial Sequence
<220> FEATURE:
<223> OTHER INFORMATION: VL region-CDR-3

<400> SEQUENCE: 7

Gln Gln Arg Ser Ser Tyr Pro Leu Thr
1               5

<210> SEQ ID NO 8
<211> LENGTH: 96
<212> TYPE: PRT
<213> ORGANISM: Artificial Sequence
<220> FEATURE:
<223> OTHER INFORMATION: VL region
<220> FEATURE:
<221> NAME/KEY: VARIANT
<222> LOCATION: 6,9,10,11,18,21,26,30,35,36,48,49,74,80
<223> OTHER INFORMATION: Xaa is any of amino acid

<400> SEQUENCE: 8

Gln Ile Val Leu Thr Xaa Ser Pro Xaa Xaa Xaa Ser Ala Ser Pro Gly
1               5                   10                  15

Glu Xaa Val Thr Xaa Thr Cys Ser Ala Xaa Ser Ser Val Xaa Tyr Met
                20                  25                  30

His Trp Xaa Xaa Gln Lys Pro Gly Thr Ser Pro Lys Leu Trp Ile Xaa
            35                  40                  45

Xaa Thr Ser Asn Leu Ala Ser Gly Val Pro Ala Arg Phe Ser Gly Ser
        50                  55                  60

Gly Ser Gly Thr Ser Tyr Ser Leu Thr Xaa Ser Arg Met Glu Ala Xaa
65                  70                  75                  80

Asp Ala Ala Thr Tyr Tyr Cys Gln Gln Arg Ser Ser Tyr Pro Leu Thr
                85                  90                  95

<210> SEQ ID NO 9
<211> LENGTH: 12
<212> TYPE: DNA
<213> ORGANISM: Artificial Sequence
<220> FEATURE:
<223> OTHER INFORMATION: TAR DNA A-site

<400> SEQUENCE: 9 cttttttgcct gt                                                          12
```

```
<210> SEQ ID NO 10
<211> LENGTH: 12
<212> TYPE: DNA
<213> ORGANISM: Artificial Sequence
<220> FEATURE:
<223> OTHER INFORMATION: TAR DNA B-site

<400> SEQUENCE: 10
tgggtctctc tg                                                          12
```